United States Patent
Yamamoto et al.

(10) Patent No.: US 8,900,638 B2
(45) Date of Patent: Dec. 2, 2014

(54) SOLID PREPARATION COMPRISING ALOGLIPTIN AND METFORMIN HYDROCHLORIDE

(75) Inventors: Kazumichi Yamamoto, Osaka (JP); Hiroyoshi Koyama, Osaka (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 312 days.

(21) Appl. No.: 12/452,705

(22) PCT Filed: Jul. 16, 2008

(86) PCT No.: PCT/JP2008/063228
§ 371 (c)(1),
(2), (4) Date: Jan. 19, 2010

(87) PCT Pub. No.: WO2009/011451
PCT Pub. Date: Jan. 22, 2009

(65) Prior Publication Data
US 2010/0136127 A1    Jun. 3, 2010
US 2011/0014299 A2    Jan. 20, 2011

(30) Foreign Application Priority Data

Jul. 19, 2007 (JP) ................................ 2007-188574

(51) Int. Cl.
*A61K 9/50* (2006.01)
*C07D 239/02* (2006.01)
(Continued)

(52) U.S. Cl.
CPC ............... *A61K 9/2018* (2013.01); *A61K 9/209* (2013.01); *A61K 45/06* (2013.01); *A61K 9/2086* (2013.01); *A61K 9/2853* (2013.01); *A61K 31/155* (2013.01); *A61K 9/2866* (2013.01); *A61K 9/2054* (2013.01); *A61K 31/513* (2013.01); *A61K 9/2077* (2013.01); *A61K 9/2027* (2013.01)
USPC ............................ 424/499; 544/312; 514/274

(58) Field of Classification Search
CPC ............ A61K 2300/00; A61K 31/155; A61K 31/513; A61K 45/06; A61K 9/2018; A61K 9/2027; A61K 9/2054; A61K 9/2077; A61K 9/2086; A61K 9/209; A61K 9/2853; A61K 9/2866; A61K 9/1652; C07D 239/54
USPC ........................... 424/499; 544/312; 514/274
See application file for complete search history.

(56) References Cited

U.S. PATENT DOCUMENTS 3,174,901 A    3/1965  Sterne
6,303,146 B1  10/2001  Bonhomme et al.
(Continued)

FOREIGN PATENT DOCUMENTS

EP    1 970 063 A1    9/2008
RU    2226396 C2      4/2004
(Continued)

OTHER PUBLICATIONS

Haines et al. (Prevention of obesity and eating disorders: a consideration of shared risk factors Health Education Research vol. 21 No. 6 2006 pp. 770-782).*
(Continued)

*Primary Examiner* — Aradhana Sasan
(74) *Attorney, Agent, or Firm* — Foley & Lardner LLP

(57) ABSTRACT

The present invention provides a solid preparation containing compound (I) [compound (I) is as defined in the specification] or a salt thereof, and metformin hydrochloride, which is useful as a therapeutic drug for diabetes and the like, and superior in the preservation stability. A solid preparation having a first part and a second part: a first part: a part containing compound (I) or a salt thereof and substantially free of metformin hydrochloride a second part: a part containing metformin hydrochloride and substantially free of compound (I) and a salt thereof.

23 Claims, 1 Drawing Sheet

Production Example 11

(51) Int. Cl.
*A61K 31/505* (2006.01)
*A61K 9/24* (2006.01)
*A61K 45/06* (2006.01)
*A61K 9/20* (2006.01)
*A61K 9/28* (2006.01)
*A61K 31/155* (2006.01)
*A61K 31/513* (2006.01)

(56) References Cited

U.S. PATENT DOCUMENTS

| | | | |
|---|---|---|---|
| 6,403,121 | B1 | 6/2002 | Adjei et al. |
| 6,524,618 | B1 * | 2/2003 | Kumar et al. ............ 424/468 |
| 6,559,188 | B1 | 5/2003 | Gatlin et al. |
| 6,930,185 | B2 | 8/2005 | Ishihara et al. |
| 7,229,986 | B2 | 6/2007 | Ishihara et al. |
| 2003/0187074 | A1 | 10/2003 | Hussain et al. |
| 2003/0224046 | A1 * | 12/2003 | Rao et al. .............. 424/468 |
| 2004/0202718 | A1 | 10/2004 | Tyebji et al. |
| 2005/0137125 | A1 | 6/2005 | Chan et al. |
| 2005/0261271 | A1 | 11/2005 | Feng et al. |
| 2005/0287207 | A1 | 12/2005 | Koike et al. |
| 2006/0094722 | A1 | 5/2006 | Yasuda et al. |
| 2007/0066635 | A1 | 3/2007 | Andres et al. |
| 2007/0264331 | A1 * | 11/2007 | Regalado et al. ........ 424/468 |
| 2008/0132542 | A1 * | 6/2008 | Lachance et al. ........ 514/326 |
| 2009/0042863 | A1 | 2/2009 | Takeuchi et al. |
| 2010/0003289 | A1 | 1/2010 | Woo et al. |

FOREIGN PATENT DOCUMENTS

| | | |
|---|---|---|
| RU | 2003126257 A | 2/2005 |
| RU | 2004108219 A | 3/2005 |
| RU | 2280447 C2 | 7/2006 |
| RU | 2286788 C2 | 11/2006 |
| RU | 2311907 C2 | 12/2007 |
| RU | 2333760 C2 | 9/2008 |
| RU | 2355386 C2 | 5/2009 |
| RU | 2357757 C2 | 6/2009 |
| RU | 2367423 C2 | 9/2009 |
| RU | 2380097 C1 | 1/2010 |
| WO | WO 97/10224 A1 | 3/1997 |
| WO | WO 99/38501 A2 | 8/1999 |
| WO | WO 01/14372 A2 | 3/2001 |
| WO | WO 01/32157 A2 | 5/2001 |
| WO | WO 01/82875 A2 | 11/2001 |
| WO | WO 01/82925 A1 | 11/2001 |
| WO | WO 01/87834 A1 | 11/2001 |
| WO | WO 01/97808 A1 | 12/2001 |
| WO | WO 03/007951 A1 | 1/2003 |
| WO | WO 2004/010375 A2 | 1/2004 |
| WO | WO 2004/031374 A2 | 4/2004 |
| WO | WO 2004/110375 A2 | 12/2004 |
| WO | WO 2005/016911 A1 | 2/2005 |
| WO | WO 2005/095381 A1 | 10/2005 |
| WO | WO 2007/033266 A2 | 3/2007 |
| WO | WO 2007/035372 A2 | 3/2007 |
| WO | WO 2007/072083 A1 | 6/2007 |
| WO | WO 2007/074884 A1 | 7/2007 |
| WO | WO 2007/078726 A2 | 7/2007 |
| WO | WO 2008/093878 A1 | 8/2008 |
| WO | WO 2008/093882 A1 | 8/2008 |

OTHER PUBLICATIONS

Opposition filed Jan. 2011, against corresponding Colombian application by Gynopharm S.A.S., with English translation, 12 pages.

Opposition filed Jan. 2011, against corresponding Colombian application by Laboratorio Franco Colombiano Lafrancol S.A., with English translation, 14 pages.

The Merck Index, An Encyclopedia of Chemicals, Drugs and Biologicals, Fourteenth Edition, 2006, "Metformin," p. 1025.

International Search Report mailed Nov. 25, 2008 in PCT/JP2008/063228, 4 pages.

Opposition Motion filed against corresponding Costa Rican patent application on Aug. 5, 2010, 7 pages, with English translation, 7 pages.

Opposition Motion filed against corresponding Ecuadorian patent application on Jul. 29, 2010, 8 pages, with English translation, 6 pages.

Observations filed May 26, 2010 in corresponding Dominican Republic patent application, 16 pages.

* cited by examiner

US 8,900,638 B2

SOLID PREPARATION COMPRISING ALOGLIPTIN AND METFORMIN HYDROCHLORIDE

CROSS-REFERENCE TO RELATED APPLICATIONS

This application is a National Stage application of PCT/JP2008/063228, filed Jul. 16, 2008, which claims priority from Japanese application JP 2007-188574, filed Jul. 19, 2007.

TECHNICAL FIELD

The present invention relates to a solid preparation superior in the preservation stability, which comprises 2-[[6-[(3R)-3-amino-1-piperidinyl]-3,4-dihydro-3-methyl-2,4-dioxo-1 (2H)-pyrimidinyl]methyl]benzonitrile (general name: alogliptin; hereinafter sometimes referred to as compound (I)) useful as a therapeutic drug for diabetes and the like, or a salt thereof, and metformin hydrochloride, and a production method thereof, as well as a method of stabilizing compound (I).

BACKGROUND OF THE INVENTION

Compound (I) or a salt thereof to be used in the present invention has been reported as an inhibitor of dipeptidyl peptidase (DPP-IV) which is an enzyme that degrades glucagon-like peptide-1 (GLP-1), a hormone enhancing insulin secretion (WO2005/095381).

A report has been documented on the administration of compound (I) or a salt thereof to be used in the present invention in combination with metformin hydrochloride (WO2007/033266).

However, a preparation comprising compound (I) or a salt thereof, and metformin hydrochloride, which is superior in the preservation stability has not been reported.

DISCLOSURE OF THE INVENTION

Problems to be Solved by the Invention

Compound (I) or a salt thereof, which is a DPP-IV inhibitor, and metformin hydrochloride are each effective for the treatment of diabetes and the like, and provision of a preparation comprising the both as active ingredients (combination of drugs) has extremely high clinical usefulness. Therefore, the present inventors started development of a solid preparation comprising compound (I) or a salt thereof, and metformin hydrochloride. In a compatibility test of compound (I) or a salt thereof, and metformin hydrochloride, no problem occurred. Surprisingly, however, when a solid preparation comprising compound (I) or a salt thereof, and metformin hydrochloride was actually produced and subjected to a preservation stability test, a related substance of compound (I) (decomposed product derived from compound (I)) was detected. In other words, a decrease in the preservation stability of compound (I) or a salt thereof in a solid preparation was confirmed. For a preparation comprising compound (I) or a salt thereof, and metformin hydrochloride as active ingredients to be provided, therefore, it is necessary to prevent a decrease in the preservation stability of compound (I) or a salt thereof in the preparation.

Means of Solving the Problems

The present inventors have conducted intensive studies in an attempt to solve the above-mentioned problems and found that a solid preparation comprising compound (I) or a salt thereof, and metformin hydrochloride, which are physically separated therein from each other, is superior in the preservation stability, and further studies resulted in the completion of the present invention. In addition, they have found that the solid preparation of the present invention shows superior dissolution property of compound (I), a salt thereof and metformin hydrochloride.

Accordingly, the present invention relates to

[1] a solid preparation comprising the following first part and second part:

first part: a part comprising compound (I) or a salt thereof and substantially free of metformin hydrochloride second part: a part comprising metformin hydrochloride and substantially free of compound (I) and a salt thereof;

[2] the solid preparation of the above-mentioned [1], further comprising an additive;

[3] the solid preparation of the above-mentioned [2], comprising about 0.5-200 mg of compound (I) or a salt thereof, and about 0.1-about 2 g of metformin hydrochloride;

[4] the solid preparation of the above-mentioned [2], comprising the first part with a shortest diameter of not less than about 100 μm in at least one part, and the second part with a shortest diameter of not less than about 100 μm in at least one part;

[5] the solid preparation of the above-mentioned [2], wherein is the first part has an average particle size of not less than about 75 μm, and the second part has an average particle size of not less than about 75 μm;

[6] the solid preparation of the above-mentioned [2], wherein the compound (I) or a salt thereof is a benzoate of compound (I);

[7] the solid preparation of the above-mentioned [2], which is a tablet;

[8] the solid preparation of the above-mentioned [2], wherein the first part and the second part are granules or tablets;

[9] the solid preparation of the above-mentioned [8], which is a capsule comprising the aforementioned granule or the aforementioned tablet;

[10] the solid preparation of the above-mentioned [2], wherein the weight ratio of compound (I) or a salt thereof contained in the first part and metformin hydrochloride contained in the second part is 1:5-1:400;

[11] the solid preparation of the above-mentioned [2], wherein the additive is a cellulose;

[12] a solid preparation obtained by compression molding of a mixture of the following first granule and second granule:

first granule: a granule comprising compound (I) or a salt thereof and substantially free of metformin hydrochloride second granule: a granule comprising metformin hydrochloride and substantially free of compound (I) and a salt thereof;

[13] the solid preparation of the above-mentioned [12], wherein the proportion of the content of the first granule with a particle size of less than 150 μm relative to the total amount of the first granule is not less than about 20 wt %, the proportion of the content of the first granule with a particle size of not less than 250 μm relative to the total amount of the first granule is not more than about 50 wt %, the proportion of the content of the second granule with a particle size of less than 150 μm relative to the total amount of the second granule is not less than about 20 wt %, and the proportion of the content of the second granule with a particle size of not less than 250 μm relative to the total amount of the second granule is not more than about 50 wt %;

[14] the solid preparation of the above-mentioned [12], herein the weight ratio of compound (I) or a salt thereof contained in the first granule and metformin hydrochloride contained in the second granule is 1:5-1:400;

[15] a solid preparation comprising the following core and layer:
  core: a core comprising metformin hydrochloride and substantially free of compound (I) and a salt thereof
  layer: a layer comprising compound (I) or a salt thereof and substantially free of metformin hydrochloride;

[16] a solid preparation comprising the following core and layer:
  core: a core comprising compound (I) or a salt thereof and substantially free of metformin hydrochloride
  layer: a layer comprising metformin hydrochloride and substantially free of compound (I) and a salt thereof;

[17] the solid preparation of the above-mentioned [15] or [16], further comprising an intermediate layer between the aforementioned core and the aforementioned layer;

[18] the solid preparation of the above-mentioned [15] or [16], wherein the aforementioned layer is formed by spray coating;

[19] the solid preparation of the above-mentioned [15] or [16], wherein the aforementioned layer is formed by compression;

[20] a solid preparation comprising the following first layer and second layer:
  first layer: a layer comprising compound (I) or a salt thereof and substantially free of metformin hydrochloride
  second layer: a layer comprising metformin hydrochloride and substantially free of compound (I) and a salt thereof;

[21] the solid preparation of the above-mentioned [20], further comprising an intermediate layer between the aforementioned first layer and the aforementioned second layer;

[22] a solid preparation comprising compound (I) or a salt thereof, and metformin hydrochloride, which shows each peak area ratio defined below of related substances RS1 to RS6 defined below of not more than 0.5% by high performance liquid chromatography analysis under the following conditions after one-month preservation at temperature 40° C.; humidity 22% RH, 33% RH, 44% RH or 57% RH; open state:

[Conditions of High Performance Liquid Chromatography Analysis]
(1) column: Zorbax SB-CN, 5 µm, inner diameter 4.6 mm×25 cm
  (manufactured by Agilent)
(2) mobile phase:
  mobile phase A: purified water/acetonitrile/trifluoroacetic acid=1900/100/1 (volume ratio)
  mobile phase B: purified water/acetonitrile/trifluoroacetic acid=100/1900/1 (volume ratio)
(3) elution gradient program:
  from 0 min to 30 min: 99/1 (mobile phase A/mobile phase B) to 75/25 (mobile phase A/mobile phase B)
  from 30 min to 50 min: 75/25 (mobile phase A/mobile phase B) to 10/90 (mobile phase A/mobile phase B)
  from 50 min to 51 min: 10/90 (mobile phase A/mobile phase B) to 99/1 (mobile phase A/mobile phase B)
  from 51 min to 60 min: 99/1 (mobile phase A/mobile phase B) (constant)
(4) flow rate: 1 ml/min
(5) detector: UV 278 nm
(6) sample temperature: about 3° C.-about 10° C.
(7) column temperature: about 20° C.-about 30° C.

[Related Substances RS1-RS6]
  related substances RS1-RS6 are derived from compound (I) or a salt thereof, and show a relative elution time of 0.60±10%, 1.08±10%, 1.30±10%, 1.49±10%, 1.52±10% and 1.62±10%, respectively, when the elution time of compound (I) is 1.00, by high performance liquid chromatography analysis under the above-mentioned conditions,

[Peak Area Ratio]
  peak area ratio shows the ratio of each peak area relative to the peak area at an assumed content of compound (I) as 100, in a chromatograph by high performance liquid chromatography analysis under the above-mentioned conditions;

[23] a solid preparation comprising compound (I) or a salt thereof, and metformin hydrochloride, wherein the compound (I) or a salt thereof is physically separated from metformin hydrochloride;

[24] a solid preparation of any one of the above-mentioned [1] to [23], which is a prophylactic or therapeutic drug for diabetes or obesity;

[25] a method of stabilizing compound (I) or a salt thereof in a solid preparation comprising compound (I) or a salt thereof, metformin hydrochloride and an additive, which comprises physically separating the compound (I) or a salt thereof from the metformin hydrochloride by the additive;

[26] a method of producing a solid preparation, comprising a step of mixing the following first granule, second granule and additive and compression molding the mixture:
  first granule: a granule comprising compound (I) or a salt thereof and substantially free of metformin hydrochloride
  second granule: a granule comprising metformin hydrochloride and substantially free of compound (I) and a salt thereof;

and the like.

Effect of the Invention

The solid preparation of the present invention is useful as a therapeutic drug for diabetes and the like, and superior in the preservation stability and dissolution property of compound (I), a salt thereof and metformin hydrochloride.

DETAILED DESCRIPTION OF THE INVENTION

Figure 1:
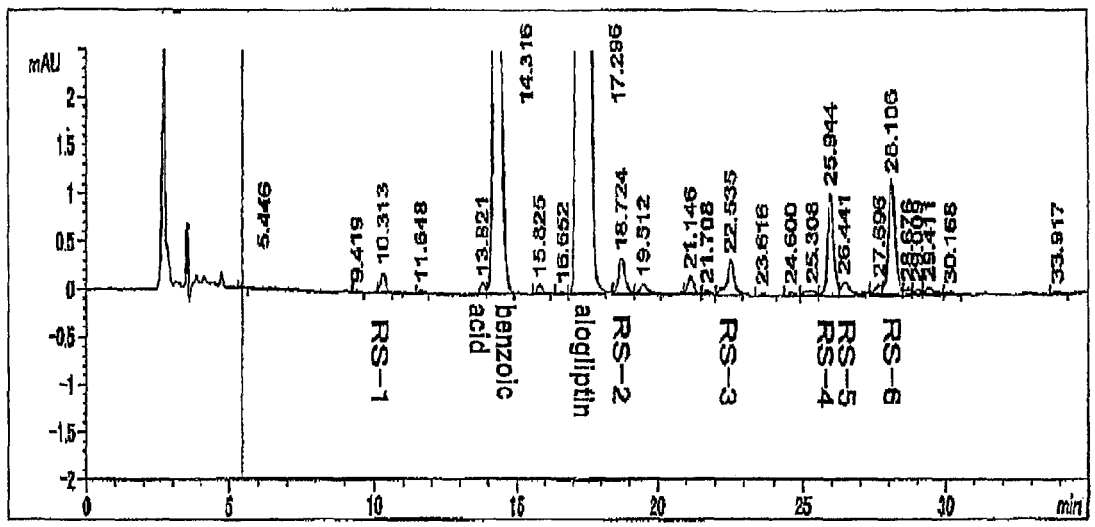
FIG. 1 is an HPLC chromatogram.

The solid preparation of the present invention is explained in detail in the following.

The first and second parts in the solid preparation of the present invention mean components that can each be present as an independent composition.

In the solid preparation of the present invention, compound (I) and a salt thereof are each physically separated from metformin hydrochloride. In the present invention, "physically separated" means that a contact of compound (I) and a salt thereof with metformin hydrochloride is inhibited, and does not necessarily mean a complete separation thereof from each other.

In other words, the solid preparation of the present invention contains the first part and the second part below:
first part: a part comprising compound (I) or a salt thereof and substantially free of metformin hydrochloride second part: a part comprising metformin hydrochloride and substantially free of compound (I) and a salt thereof (1) First Part The first part in the present invention is a part (or a pharmaceutical composition) comprising compound (I) or a salt thereof and substantially free of metformin hydrochloride.

Being "substantially free of metformin hydrochloride" means that the content of metformin hydrochloride is 0-3 parts by weight, preferably 0-1 part by weight, relative to 100 parts by weight of the total of the first part in the present invention.

Examples of the salt of compound (I) include a pharmacologically acceptable salt, such as salts with inorganic acids, salts with organic acids, salts with basic or acidic amino acids and the like.

Examples of the salts with inorganic acids include salts with hydrochloric acid, hydrobromic acid, nitric acid, sulfuric acid, phosphoric acid and the like.

Examples of the salts with organic acids include salts with benzoic acid, formic acid, acetic acid, trifluoroacetic acid, fumaric acid, oxalic acid, tartaric acid, maleic acid, citric acid, succinic acid, malic acid, methanesulfonic acid, benzenesulfonic acid, p-toluenesulfonic acid and the like.

Examples of the salts with basic amino acids include salts with arginine, lysine, ornithine and the like, and examples of the salts with acidic amino acids include salts with aspartic acid, glutamic acid and the like.

Preferable examples of the salts of compound (I) include salts with benzoic acid, trifluoroacetic acid, p-toluenesulfonic acid, and the like, with preference given to a salt with benzoic acid.

Compound (I) or a salt thereof is preferably a benzoate of compound (I), trifluoroacetate of compound (I), p-toluenesulfonate of compound (I) or hydrochloride of compound (I), more preferably a benzoate of compound (I) (sometimes to be abbreviated as compound (IA) in the present specification).

The content of compound (I) or a salt thereof is, as compound (I) (i.e., as a free form), preferably 0.1-90 parts by weight, more preferably 0.5-80 parts by weight, still more preferably 1-70 parts by weight, particularly preferably 2-50 parts by weight, relative to 100 parts by weight of the total of the first part in the present invention.

The above-mentioned first part may have any shape or size as long as it can form a solid preparation together with the below-mentioned second part, and can be administered (preferably orally administered) to living organisms.

In addition, the first part may have any inside structure, and the inside may be uniform or nonuniform. The form of the first part may be, for example, a tablet part, or a physically independent granule or tablet.

In consideration of the preservation stability, the solid preparation of the present invention preferably contains, in at least one part, the first part having a shortest diameter of not less than about 100 μm to physically separate compound (I) and a salt thereof from metformin hydrochloride. While the upper limit of the shortest diameter is not particularly limited, it is generally not more than about 2 mm for oral dosage forms.

The shortest diameter means the shortest axis diameter. When the first part is a granule, for example, it means the shortest axis diameter of the granule. The short axis diameter can be measured using a microscope and the like. The microscope only needs to be able to measure the size of 100 μm level.

The shortest diameter of the first part means the shortest diameter of the first part contained in a solid preparation. For easy measurement, it may be the shortest diameter of the first part before constitution of the solid preparation.

For preservation stability, the solid preparation of the present invention preferably contains a first part having an average particle size of not less than about 75 μm (preferably not less than about 100 μm) to physically separate compound (I) and a salt thereof from metformin hydrochloride. While the upper limit of the average particle size of the first part is not particularly limited, it is generally about not more than 1.5 mm for oral dosage forms.

In the present invention, the particle size is measured by a sieving method (Powder—Theory and Application—, p. 475, 1979, Maruzen). The average particle size is calculated based on the average aperture of the corresponding sieve and weight distribution of the particles. That is, it is obtained by arithmetic averaging of the product of an average and each weight.

Here, the average particle size of the first part means an average particle size of the first part contained in a solid preparation. For easy measurement, it may be an average particle size of the first part before constitution of the solid preparation.

The above-mentioned first part may contain an additive conventionally used in the field of pharmaceutical preparation. Examples of the additive include excipients, disintegrant, binder, lubricant, colorant, pH adjuster, surfactant, stabilizer, acidulant, flavor, glidant, coating base, coating additive and the like. Unless particularly indicated, these additives are used in an amount conventionally employed in the field of pharmaceutical preparation.

The above-mentioned first part can be produced by a method known per se according to the dosage form of the solid preparation of the present invention.

Preferable examples of the excipient include sugars such as lactose, sucrose, fructose and glucose; sugar alcohols such as erythritol, mannitol, sorbitol, xylitol, maltitol and the like; starches such as cornstarch, potato starch, wheat starch, rice starch, partly pregelatinized starch, pregelatinized starch, porous starch and the like; celluloses such as crystalline cellulose (e.g., microcrystalline cellulose), powdered cellulose, low-substituted hydroxypropylcellulose and the like; anhydrous calcium phosphate, precipitated calcium carbonate, calcium silicate and the like. Among these, mannitol, crystalline cellulose and the like are preferable.

The amount of the excipient to be used is preferably 1-95 parts by weight, more preferably 5-90 parts by weight, relative to 100 parts by weight of the above-mentioned first part.

Preferable examples of the disintegrant include crospovidone, carboxymethylcellulose, calcium carboxymethylcellulose, sodium carboxymethyl starch, croscarmellose sodium, low-substituted hydroxypropylcellulose, hydroxypropyl starch and the like.

When the disintegrant is used, the amount thereof to be used is preferably 0.1-30 parts by weight, more preferably 1-20 parts by weight, still more preferably 2-10 parts by weight, relative to 100 parts by weight of the above-mentioned is first part.

Preferable examples of the binder include crystalline cellulose (e.g., crystalline cellulose), hydroxypropylcellulose [e.g., grades: L, SL, SL-T, SSL (trade name); Nippon Soda Co., Ltd.], hydroxypropylmethylcellulose [e.g., Metolose TC-5 (grades: MW, E, EW, R, RW) (trade name); Shin-Etsu Chemical Co., Ltd.], polyvinylpyrrolidone, gum arabic and the like. Among these, crystalline cellulose, hydroxypropylcellulose, hydroxypropylmethylcellulose, polyvinylpyrrolidone and the like are preferable.

The amount of the binder to be used is preferably 0.1-40 parts by weight, more preferably 0.5-30 parts by weight, still more preferably 1-20 parts by weight, relative to 100 parts by weight of the above-mentioned first part.

Preferable examples of the lubricant include magnesium stearate, calcium stearate, talc, sucrose esters of fatty acids, sodium stearyl fumarate and the like.

When the lubricant is used, the amount thereof to be used is preferably 0.01-10 parts by weight, more preferably 0.05-5 parts by weight, relative to 100 parts by weight of the above-mentioned first part.

Preferable examples of the colorant include food colors such as Food Color Yellow No. 5, Food Color Red No. 2, Food Color Blue No. 2 and the like, food lake colors, ferric oxide, yellow ferric oxide and the like.

Preferable examples of the pH adjuster include citric acid or a salt thereof, phosphoric acid or a salt thereof, carbonic acid or a salt thereof, tartaric acid or a salt thereof, fumaric acid or a salt thereof, acetic acid or salt thereof, amino acid or a salt thereof and the like.

Preferable examples of the surfactant include sodium lauryl sulfate, polysorbate 80, polyoxyethylene(160)polyoxypropylene(30)glycol and the like.

Preferable examples of the stabilizer include tocopherol, tetrasodium edetate, nicotinic acid amide, cyclodextrins and the like.

Preferable examples of the acidulant include ascorbic acid, citric acid, tartaric acid, malic acid and the like.

Preferable examples of the flavor include menthol, peppermint oil, lemon oil, vanillin and the like.

Preferable examples of the glidant include light anhydrous silicic acid, hydrated silicon dioxide and the like.

Preferable examples of the coating base include sugar coating base, aqueous film coating base, enteric film coating base, sustained-release film coating base and the like.

As the sugar coating base, sucrose is used. Furthermore, one or more kinds selected from talc, precipitated calcium carbonate, gelatin, gum arabic, pullulan, carnauba wax and the like may be used in combination.

Examples of the aqueous film coating base include cellulose polymers such as hydroxypropylcellulose [e.g., grades: L, SL, SL-T, SSL (trade name); Nippon Soda Co., Ltd.], hydroxypropylmethylcellulose [e.g., MetoloseTC-5 (grades: MW, E, EW, R, RW) (trade name); Shin-Etsu Chemical Co., Ltd.]], hydroxyethylcellulose, methylhydroxyethylcellulose and the like; synthetic polymers such as polyvinyl acetal diethylaminoacetate, aminoalkylmethacrylate copolymer E [Eudragit E (trade name)], polyvinylpyrrolidone and the like; polysaccharides such as pullulan and the like, and the like.

Examples of the enteric film coating base include cellulose polymers such as hydroxypropylmethylcellulose phthalate, hydroxypropylmethylcellulose acetate succinate, carboxymethylethylcellulose, cellulose acetate phthalate and the like; acrylic acid polymers such as methacrylic acid copolymer L [Eudragit L (trade name)], methacrylic acid copolymer LD [Eudragit L-30D55 (trade name)], methacrylic acid copolymer S [Eudragit S (trade name)] and the like; naturally occurring substances such as shellac and the like; and the like.

Examples of the sustained-release film coating base include cellulose polymers such as ethylcellulose and the like; acrylic acid polymers such as aminoalkyl methacrylate copolymer RS [Eudragit RS (trade name)], ethyl acrylate•methacrylic acid methyl copolymer suspension [Eudragit NE (trade name)] and the like; and the like.

Preferable examples of the coating additive include light shielding agents and/or colorants such as titanium dioxide, talc, ferric oxide, yellow ferric oxide and the like; plasticizers such as polyethylene glycol [e.g., macrogol 6000 (trade name)], triethyl citrate, castor oil, polysorbates and the like; organic acids such as citric acid, tartaric acid, malic acid, ascorbic acid and the like; sugars and sugar alcohols such as lactose, mannitol and the like; and the like.

The above-mentioned additive may be a mixture of two or more kinds at an appropriate ratio.

The above-mentioned first part is preferably a part containing compound (I) or a salt thereof (preferably a benzoate of compound (I)); an excipient (preferably mannitol, and celluloses (more preferably crystalline cellulose)); and a binder (preferably hydroxypropylcellulose, hydroxypropylmethylcellulose, polyvinylpyrrolidone).

(2) Second Part

The second part in the present invention is a part (pharmaceutical composition) comprising metformin hydrochloride and substantially free of compound (I) and a salt thereof.

Being "substantially free of compound (I) or a salt thereof" means that the content of compound (I) or a salt thereof is 0-1 part by weight, preferably 0-0.5 part by weight, more preferably 0-0.1 part by weight, relative to 100 parts by weight of the total of the second part in the present invention.

The content of the metformin hydrochloride is preferably 10-99 parts by weight, more preferably 20-98 parts by weight, still more preferably 30-95 parts by weight, relative to 100 parts by weight of the above-mentioned second part.

The above-mentioned second part may have any shape or size as long as it can form a solid preparation together with the aforementioned first part, and can be administered (preferably orally administered) to living organisms. The form of the second part may be, for example, a tablet part, or a physically independent granule or tablet.

In addition, the second part may have any inside structure, and the inside may be uniform or nonuniform.

In consideration of the preservation stability, the solid preparation of the present invention preferably contains, in at least one part, the second part having a shortest diameter of not less than about 100 µm to physically separate compound (I) and a salt thereof from metformin hydrochloride. While the upper limit of the shortest diameter is not particularly limited, it is generally not more than about 2 mm for oral dosage forms.

The shortest diameter means the shortest axis diameter. When the second part is a granule, for example, it means the shortest axis diameter of the granule. The short axis diameter can be measured using a microscope and the like. The microscope only needs to be able to measure the size of 100 µm level.

The shortest diameter of the second part means the shortest diameter of the second part contained in a solid preparation. For easy measurement, it may be the shortest diameter of the second part before constitution of the solid preparation.

For preservation stability, the solid preparation of the present invention preferably contains a second part having an average particle size of not less than about 75 µm (preferably not less than about 100 µm) to physically separate compound (I) and a salt thereof from metformin hydrochloride. While the upper limit of the average particle size of the second part is not particularly limited, it is generally about not more than 1.5 mm for oral dosage forms.

The calculation of the particle size of the second part and average particle size is as defined in the first part.

Here, the average particle size of the second part means an average particle size of the second part contained in a solid preparation. For easy measurement, it may be an average particle size of the second part before constitution of the solid preparation.

The above-mentioned second part may contain an additive conventionally used in the field of pharmaceutical preparation and can be produced according to a known method. As the additive, those mentioned for the above-mentioned first part can be employed. Unless particularly indicated, these additives are used in an amount conventionally employed in the field of pharmaceutical preparation.

The above-mentioned second part can be produced by a method known per se according to the dosage form of the solid preparation of the present invention.

The amount of the excipient to be used as an additive for the second part is preferably 1-90 parts by weight, more preferably 3-80 parts by weight, still more preferably 5-70 parts by weight, relative to 100 parts by weight of the above-mentioned second part.

When a disintegrant is used as an additive for the second part, the amount thereof to be used is preferably 0.1-30 parts by weight, more preferably 1-20 parts by weight, still more preferably 2-10 parts by weight, relative to 100 parts by weight of the above-mentioned second part.

The amount of the binder to be used as an additive for the second part is preferably 0.1-30 parts by weight, more preferably 0.5-20 parts by weight, still more preferably 1-10 parts by weight, relative to 100 parts by weight of the above-mentioned second part.

When the lubricant is used as an additive for the second part, the amount thereof to be used is preferably 0.01-10 parts by weight, more preferably 0.05-5 parts by weight, relative to 100 parts by weight of the above-mentioned second part.

The amount of other additives to be used in the second part is the amount conventionally used in the field of pharmaceutical preparation.

The above-mentioned second part is preferably a part containing metformin hydrochloride; an excipient (preferably celluloses (more preferably crystalline cellulose)); and a binder (preferably polyvinylpyrrolidone).

The content weight ratio (second part/first part) of the first part and the second part in the solid preparation of the present invention is preferably 0.01-100, more preferably 0.5-80, still more preferably 2-40.

The content weight ratio of the compound (I) or a salt thereof contained in the first part and metformin hydrochloride contained in the second part (compound (I) or salt:metformin hydrochloride) in the solid preparation of the present invention is preferably 1:5-1:400, more preferably 1:15-1:300, still more preferably 1:25-1:200.

The compound (I) and metformin may be solvates (e.g., hydrates) or non-solvates (e.g., non-hydrate).

In addition, compound (I) may be labeled with an isotope (e.g., $^{3}H$, $^{14}C$, $^{35}S$, $^{125}I$).

Furthermore, it may be a deuterium converter wherein $^{1}H$ is converted to $^{2}H(D)$.

The first part and the second part can be produced by a known method according to the forms thereof or the dosage form of the solid preparation of the present invention.

In addition, the solid preparation of the present invention may have an inactive intermediate layer between the first part and the second part. The intermediate layer contains, for example, the above-mentioned coating base and coating additive. The intermediate layer preferably contains a water-soluble film coating base (preferably hydroxypropylmethylcellulose) and a light shielding agent and/or a colorant (preferably talc).

When the solid preparation of the present invention has an intermediate layer, the intermediate layer is formed at the ratio of preferably 0.1-500 parts by weight, more preferably 1-100 parts by weight, still more preferably 10-50 parts by weight, relative to 100 parts by weight of the first part.

When the solid preparation of the present invention has such an intermediate layer, an adverse influence (decreased storage or chemical stability such as time-course decomposition of active ingredients, decreased activity and the like, decreased dissolution stability such as time-course changes in the active ingredient dissolution pattern and the like, and the like) caused by the interaction of active ingredients can be suppressed more effectively.

In addition, an additive conventionally used in the pharmaceutical field may be further added after mixing the first part and the second part.

Specific embodiments of the solid preparation of the present invention include

[I] tablet

[1] A solid preparation obtained by compression molding of a mixture of the following first granule and second granule (sometimes to be abbreviated as compression-molded tablet in the present specification)

first granule: a granule comprising compound (I) or a salt thereof and substantially free of metformin hydrochloride second granule: a granule comprising metformin hydrochloride and substantially free of compound (I) and a is salt thereof.

For easy mixing, it is preferable that the proportion of the content of the first granule with a particle size of less than 150 μm relative to the total amount of the first granule be not less than about 20 wt %, the proportion of the content of the first granule with a particle size of not less than 250 μm relative to the total amount of the first granule be not more than about 50 wt %, the proportion of the content of the second granule with a particle size of less than 150 μm relative to the total amount of the second granule be not less than about 20 wt %, and the proportion of the content of the second granule with a particle size of not less than 250 μm relative to the total amount of the second granule be not more than about 50 wt %.

The weight ratio of the compound (I) or a salt thereof contained in the first granule and metformin hydrochloride contained in the second granule (compound (I) or a salt: metformin hydrochloride) is preferably 1:5-1:400, more preferably 1:15-1:250, still more preferably 1:25-1:125.

The weight ratio of each particle size can be determined by sieving granules (about 50 g) using a 30 mesh (aperture 500 μm), 42 mesh (aperture 355 μm), 60 mesh (aperture 250 μm), or 100 mesh (aperture 150 μm), and measuring the weight of the granules remaining on each sieve and the weight of the granules that passed through a 100 mesh sieve.

[2] A solid preparation comprising the following core and layer (sometimes to be abbreviated as "coated tablet (A)" in the present specification)

core: a core comprising metformin hydrochloride and substantially free of compound (I) and a salt thereof (sometimes to be abbreviated as "inner core comprised of the second part" in the present specification)

layer: a layer comprising compound (I) or a salt thereof and substantially free of metformin hydrochloride (sometimes to be abbreviated as "outer layer comprised of the first part" in the present specification)

[3] A solid preparation comprising the following core and layer (sometimes to be abbreviated as "coated tablet (B)" in the present specification)

core: a core comprising compound (I) or a salt thereof and substantially free of metformin hydrochloride (sometimes to be abbreviated as "inner core comprised of the first part" in the present specification)

layer: a layer comprising metformin hydrochloride and substantially free of compound (I) and a salt thereof (sometimes to be abbreviated as "outer layer comprised of the second part" in the present specification);

[4] A solid preparation comprising the following first layer and second layer (sometimes to be abbreviated as a "multilayer tablet" of the present invention in the present specification)

first layer: a layer comprising compound (I) or a salt thereof and substantially free of metformin hydrochloride second layer: a layer comprising metformin hydrochloride and substantially free of compound (I) and a salt thereof;

[II] A capsule comprising the first part and the second part, which are each a granule or a tablet (sometimes to be abbreviated as a capsule of the present invention);

[III] A powder pouch comprising the first part and the second part, which are each a granule or a tablet (sometimes to be abbreviated as the powder pouch of the present invention) can be exemplified.

The compression-molded tablet of the present invention can be produced, for example, according to the following production step.

(1) Compound (I) or a salt thereof is granulated with an additive as necessary, and dried, sieved and the like as necessary to give the first granule. The additive is preferably an excipient (preferably mannitol and celluloses (more preferably crystalline cellulose)); a binder (preferably polyvinylpyrrolidone) and the like.

The first granule can be preferably produced by the following production step.

Compound (I) or a salt thereof (preferably benzoate of compound (I)), and an excipient (preferably mannitol and celluloses (more preferably crystalline cellulose)) are granulated using a dispersion liquid of a binder (preferably polyvinylpyrrolidone) in a solvent (e.g., water, acetone, ethyl alcohol, propyl alcohol, and a mixture of these at an appropriate ratio; preferably water).

Here, the dispersion liquid may be any solution or suspension, and the "dispersion liquid" in the present specification includes both solution and suspension.

(2) On the other hand, metformin hydrochloride is granulated with an additive as necessary, and dried, sieved and the like as necessary to give the second granule. The additive is preferably an excipient (preferably celluloses (more preferably crystalline cellulose)); a binder (preferably polyvinylpyrrolidone) and the like.

The second granule can be preferably produced by the following production step.

Metformin hydrochloride; and an excipient (preferably celluloses (more preferably crystalline cellulose)) are granulated using a dispersion liquid of a binder (preferably polyvinylpyrrolidone) in a solvent (e.g., water, acetone, ethyl alcohol, propyl alcohol, and a mixture of these at an appropriate ratio; preferably water).

(3) The obtained first granule and second granules are mixed with a further additive as necessary. Said additive is preferably an excipient (preferably celluloses (crystalline cellulose, powdered cellulose, low-substituted hydroxypropylcellulose), more preferably crystalline cellulose [e.g., CEOLUS KG802, CEOLUS KG-1000, CEOLUS PH-F20 (trade name); Asahi Kasei Corporation]); and a binder (preferably polyvinylpyrrolidone), a disintegrant (preferably crospovidone [e.g., Kollidon CL, Kollidon CL-F, Kollidon CL-SF (trade name); BASF]), and a lubricant (preferably magnesium stearate) and the like.

In consideration of tablet hardness and dissolution property, the excipient is preferably CEOLUS KG-1000 and the disintegrant is preferably Kollidon CL-F.

(4) The obtained mixture is compression molded.

The coated tablet (A) of the present invention can be produced, for example, by the following production steps.

The inner core made of the second part can be produced, for example, by granulating metformin hydrochloride together with, where necessary, an additive. After granulation, an operation such as drying, sizing, and the like may be performed as necessary.

The additive is preferably an excipient (preferably crystalline cellulose); a binder (preferably polyvinylpyrrolidone), a disintegrant (preferably crospovidone), a lubricant (preferably magnesium stearate) and the like.

The inner core made of the above-mentioned second part can be preferably produced by the following production steps.

(1) metformin hydrochloride; the excipient (preferably crystalline cellulose) is granulated using a dispersion liquid of a binder (preferably polyvinylpyrrolidone) in a solvent (e.g., water, acetone, ethyl alcohol, propyl alcohol, and a mixture of these at an appropriate ratio; preferably water).

(2) The obtained granulated product is dried and sieved, and the obtained granule and an excipient (preferably crystalline cellulose), a disintegrant (preferably crospovidone) and a lubricant (preferably magnesium stearate) are mixed.

(3) The obtained mixture is compression molded.

On the other hand, the outer layer made of the first part can be produced, for example, by coating compound (I) or a salt thereof (preferably benzoate of compound (I)) together with, where necessary, an additive to the above-mentioned first part.

The coating can be performed, for example, by compression molding, coating and the like. The additive is preferably an excipient (preferably mannitol) and a binder (preferably hydroxypropylcellulose) and the like.

The above-mentioned outer layer made of the first part can be preferably produced according to the following production steps.

The inner core made of the second part is coated with a dispersion liquid of compound (I) or a salt thereof (preferably benzoate of compound (I)), an excipient (preferably mannitol) and a binder (preferably hydroxypropylcellulose) in a solvent (e.g., water, acetone, ethyl alcohol, propyl alcohol, and a mixture of these at an appropriate ratio; preferably water).

During production of coated tablet (A), it is preferable to form an inactive intermediate layer between an inner core and an outer layer to avoid a direct contact of them. The intermediate layer contains, for example, the above-mentioned coating base and a coating additive. The intermediate layer preferably contains an aqueous film coating base (preferably hydroxypropylmethylcellulose) and light shielding agent and/or colorant (preferably talc).

In the above-mentioned coated tablet (A), the outer layer is formed in a proportion of preferably 0.1-100 parts by weight, more preferably 1-50 parts by weight, still more preferably 3-30 parts by weight, relative to 100 parts by weight of the inner core.

In the above-mentioned coated tablet (A), moreover, the intermediate layer is formed in a proportion of preferably 0.1-30 parts by weight, more preferably 0.5-20 parts by weight, still more preferably 1-5 parts by weight, relative to 100 parts by weight of the inner core.

The above-mentioned coated tablet (B) can be produced in the same manner as coated tablet (A) except that the first part is used as the inner core and the second part is used as the outer layer.

In the above-mentioned coated tablet (B), the outer layer is formed in a proportion of preferably 1-300 parts by weight, more preferably 5-200 parts by weight, still more preferably 10-80 parts by weight, relative to 100 parts by weight of the inner core.

The multi-layer tablet of the present invention can be produced, for example, according to the following production steps.
(a) Compound (I) or a salt thereof is mixed with the above-mentioned additive as necessary and granulated as necessary to give the composition for the above-mentioned first layer.
(b) Metformin hydrochloride is mixed with the above-mentioned additive as necessary and granulated as necessary to give a composition for the above-mentioned second layer.
(c) When an inactive intermediate layer is to be formed between the first layer and the second layer to avoid direct contact of each layer, the above-mentioned additives such as excipient, binder and the like are mixed as necessary, and further granulated as necessary to give a composition for the intermediate layer.
(d) The composition for the first layer, the composition for the intermediate layer when desired, and the composition for the second layer are laminated and compression molded.

In the above-mentioned multi-layer tablet, the second layer can be formed in a proportion of preferably 1-2000 parts by weight, more preferably 5-1000 parts by weight, still more preferably 10-500 parts by weight, relative to 100 parts by weight of the first layer.

In the above-mentioned multi-layer tablet, moreover, the intermediate layer can be formed in a proportion of preferably 0.1-1000 parts by weight, more preferably 1-500 parts by weight, still more preferably 10-300 parts by weight, relative to 100 parts by weight of the first layer.

A capsule of the present invention can be produced by, for example, filling a capsule (e.g., gelatin capsule) with the above-mentioned mixture of the first granule and the second granule, the above-mentioned compression-molded tablet, the above-mentioned coated tablet (A) or (B), or the above-mentioned multi-layer tablet.

Particularly preferable examples of the solid preparation of the present invention include the above-mentioned compression-molded tablets.

In addition, film coating preparations produced by film coating the above-mentioned compression-molded tablet, the above-mentioned coated tablet (A) or (B), and the above-mentioned multi-layer tablet with the above-mentioned coating base and coating additive are also encompassed in the solid preparation of the present invention.

In addition, the solid preparation of the present invention may be stamped or printed with letters for discrimination, or has a separating line for dividing the tablet.

From the aspects of easy administration, preparation strength and the like, the solid preparation of the present invention is preferably film-coated.

The operations such as mixing, compression molding, coating and the like in the aforementioned production step are performed according to a method conventionally used in the technical field of pharmaceutical preparations.

The mixing is performed, for example, using a mixer such as a V-type mixer, a tumbler mixer and the like; and a granulation machine such as a high speed mixer granulator, a fluidized granulating dryer, an extrusion granulator, a roller compactor and the like.

Compression molding is performed, for example, using a single punch tableting machine, a rotary tableting machine and the like.

When a single punch tableting machine, a rotary tableting machine and the like are used, a tableting pressure of generally 1-35 kN/cm$^2$ (preferably 5-35 kN/cm$^2$) is preferably employed. Furthermore, to prevent capping, a tapered die is preferably used.

The coating is performed, for example, using a film coating apparatus and the like.

The solid preparation of the present invention preferably contains about 0.5-200 mg of compound (I) or a salt thereof, and about 0.1-about 2 g of metformin hydrochloride.

The solid preparation of the present invention more preferably contains about 1-100 mg of compound (I) or a salt thereof, and about 0.5-about 1.5 g of metformin hydrochloride.

The solid preparation of the present invention can be safely administered orally or parenterally to a mammal (e.g., mouse, rat, rabbit, cat, dog, bovine, horse, monkey, human).

The solid preparation of the present invention and each active ingredient contained in the solid preparation are useful for the prophylaxis or treatment of, for example, diabetes [e.g., type 1 diabetes, type 2 diabetes, type 1.5 diabetes (LADA (Latent Autoimmune Diabetes in Adults)), gestational diabetes, diabetes with impaired insulin secretion, to obese diabetes, impaired glucose tolerance (IGT), IFG (Impaired Fasting Glucose), IFG (Impaired Fasting Glycaemia)], diabetic complications [e.g., neuropathy, nephropathy, retinopathy, cataract, macroangiopathy, arteriosclerosis, osteopenia, hyperosmolar diabetic coma, infections (e.g., is respiratory infection, urinary tract infection, gastrointestinal infection, dermal soft tissue infections, inferior limb infection), diabetic gangrene, xerostomia, hypacusis, cerebrovascular disorder, peripheral blood circulation disorder], obesity, hyperlipidemia (e.g., hypertriglyceridemia, hypercholesterolemia, hyperLDL-cholesterolemia, hypoHDL-cholesterolemia, postprandial hyperlipemia), arteriosclerosis (e.g., atherosclerosis), hypertension, myocardial infarction, angina pectoris, cerebrovascular disorder (e.g., cerebral infarction, cerebral apoplexy), insulin resistance syndrome, syndrome X, dysmetabolic syndrome and the like. In addition, the solid preparation of the present invention is also useful for secondary prevention of the above-mentioned various diseases (e.g., secondary prevention of cardiovascular event such as myocardial infarction and the like) or suppression of progression [e.g., suppression of progression from impaired glucose tolerance to diabetes; suppression of progression from diabetes to diabetic complications (preferably diabetic neuropathy, diabetic nephropathy, diabetic retinopathy, arteriosclerosis)].

The dose of the solid preparation of the present invention only needs to be an effective amount of compound (I) and metformin contained in the solid preparation.

Here, the effective amount of compound (I) or a salt thereof is, for example, generally 1-100 mg/day, preferably 3-50 mg/day, as compound (I) for an adult (body weight 60 kg).

In the case of metformin hydrochloride, the effective amount thereof is generally 50-5000 mg/day, preferably 250-2550 mg/day, for an adult (body weight 60 kg).

The administration frequency of the solid preparation of the present invention to the aforementioned mammals for one day is preferably 1-3 times a day, more preferably twice a day.

Particularly preferable examples of the solid preparation of the present invention include
a compression-molded tablet containing 8.5 mg of a benzoate of compound (I) and 1000 mg of metformin hydrochloride per tablet;
a compression-molded tablet containing 8.5 mg of a benzoate of compound (I) and 500 mg of metformin hydrochloride per tablet;

a compression-molded tablet containing 17 mg of a benzoate of compound (I) and 500 mg of metformin hydrochloride per tablet; and
a compression-molded tablet containing 17 mg of a benzoate of compound (I) and 1000 mg of metformin hydrochloride per tablet.

Since the solid preparation of the present invention has a constitution wherein compound (I) or a salt thereof, and metformin hydrochloride are physically separated from each other, it is superior in the preservation stability. The solid preparation of the present invention preferably shows each peak area ratio defined below of related substances RS1 to RS6 defined below of not more than 0.5% (more preferably not more than 0.2%) by high performance liquid chromatography analysis under the following conditions after one-month preservation at temperature 40° C.; humidity 22% RH, 33% RH, 44% RH or 57% RH; open state.

The analysis can be performed according to the method described in the following Experimental Example 1.
[Conditions of High Performance Liquid Chromatography Analysis]
(1) column: Zorbax SB-CN, 5 μm, inner diameter 4.6 mm×25 cm
    (manufactured by Agilent)
(2) mobile phase:
    mobile phase A: purified water/acetonitrile/trifluoroacetic acid=1900/100/1 (volume ratio)
    mobile phase B: purified water/acetonitrile/trifluoroacetic acid=100/1900/1 (volume ratio)
(3) elution gradient program:
    from 0 min to 30 min: 99/1 (mobile phase A/mobile phase B) to 75/25 (mobile phase A/mobile phase B)
    from 30 min to 50 min: 75/25 (mobile phase A/mobile phase B) to 10/90 (mobile phase A/mobile phase B)
    from 50 min to 51 min: 10/90 (mobile phase A/mobile phase B) to 99/1 (mobile phase A/mobile phase B)
    from 51 min to 60 min: 99/1 (mobile phase A/mobile phase B) (constant)
(4) flow rate: 1 ml/min
(5) detector: UV 278 nm
(6) sample temperature: about 3° C.-about 10° C.
(7) column temperature: about 20° C.-about 30° C.
[Related Substances RS1-RS6]

In the present specification, related substances RS1-RS6 are derived from compound (I) or a salt thereof, and show a relative elution time of 0.60±10%, 1.08±10%, 1.30±10%, 1.49±10%, 1.52±10% and 1.62±10%, respectively, when the elution time of compound (I) is 1.00, by high performance liquid chromatography analysis under the above-mentioned conditions. The peaks of these substances are not seen in the preservation tests of the solid preparations containing metformin hydrochloride and free of compound (I) and a salt thereof. Utilizing this, related substances of compound (I) can be identified.

Here, a shift range (±10%) is formed for each relative elution time of the related substances of compound (I), since the elution time varies depending on the measurement conditions such as column temperature, column lot difference, constitution ratio of the mobile phase and the like. When a variation is found in the relative elution time of a related substance, variations are also found in the relative elution time of other related substances. However, the order of elution of RS1-6 does not change.

In a high performance liquid chromatography analysis under the above-mentioned conditions, related substances RS-1-6 and compound (I) are eluted in the order of related substance RS-1, compound (I), related substance RS-2, related substance RS-3, related substance RS-4, related substance RS-5 and related substance RS-6. FIG. 1 shows an embodiment of chromatograph actually analyzed. In the chromatogram of FIG. 1, the peaks of related substance RS-1, benzoic acid, compound (I), related substance RS-2, related substance RS-3, related substance RS-4, related substance RS-5 and related substance RS-6 can be observed.
[Peak Area Ratio]

The peak area ratio shows the ratio of each peak area relative to the peak area at an assumed content of compound (I) as 100, in a chromatograph by high performance liquid chromatography analysis under the above-mentioned conditions.

Here, the assumed content of compound (I) means the content of compound (I) assumed by a manufacturer during production of a solid preparation. It is a content of compound (I) (namely, a free form) calculated from the weight of compound (I) or a salt thereof and the weights of other components. The content corresponds to the amount of the active ingredient indicated on a label or a package insert of a product.

The solid preparation of the present invention and each active ingredient contained in the solid preparation can be used in combination with one or more pharmaceutical agents selected from a therapeutic agent for diabetes, a therapeutic agent for diabetic complications, a therapeutic agent for hyperlipidemia, an antihypertensive agent, an antiobesitic agent, a diuretic, an antithrombotic agent and the like (hereinafter sometimes to be abbreviated as a combination drug).

Examples of the therapeutic agent for diabetes include insulin preparations (e.g., animal insulin preparation extracted from the pancreas of bovine or swine; human insulin preparation synthesized by genetic engineering using *Escherichia coli* or yeast; zinc insulin; protamine zinc insulin; fragment or derivative of insulin (e.g., INS-1), oral insulin preparation), insulin sensitizers (e.g., pioglitazone or a salt thereof (preferably hydrochloride), rosiglitazone or a salt thereof (preferably maleate), tesaglitazar, ragaglitazar, muraglitazar, edaglitazone, metaglidasen, naveglitazar, AMG-131, THR-0921), α-glucosidase inhibitors (e.g., voglibose, acarbose, miglitol, emiglitate), biguanides (e.g., buformin or salts thereof (e.g., hydrochloride, fumarate, succinate)), insulin secretagogues [sulfonylurea (e.g., tolbutamide, glibenclamide, gliclazide, chlorpropamide, tolazamide, acetohexamide, glyclopyramide, glimepiride, glipizide, glybuzole), repaglinide, nateglinide, mitiglinide or calcium salt hydrate thereof], dipeptidyl peptidase IV inhibitors other than compound (I) (e.g., vildagliptin, sitagliptin, saxagliptin, T-6666, TS-021), β3 agonists (e.g., AJ-9677), GPR40 agonists, GLP-1 receptor agonists [e.g., GLP-1, GLP-1MR agent, N,N-2211, AC-2993 (exendin-4), BIM-51077, Aib(8,35) hGLP-1(7,37)NH$_2$, CJC-1131], amylin agonists (e.g., pramlintide), phosphotyrosine phosphatase inhibitors (e.g., sodium vanadate), gluconeogenesis inhibitors (e.g., glycogen phosphorylase inhibitor, glucose-6-phosphatase inhibitor, glucagon antagonist), SGLUT (sodium-glucose cotransporter) inhibitors (e.g., T-1095), 11β-hydroxysteroid dehydrogenase inhibitors (e.g., BVT-3498), adiponectin or agonists thereof, IKK inhibitors (e.g., AS-2868), leptin resistance improving drugs, somatostatin receptor agonists, glucokinase activators (e.g., Ro-28-1675), GIP (Glucose-dependent insulinotropic peptide) and the like.

Examples of the therapeutic agents for diabetic complications include aldose reductase inhibitors (e.g., tolrestat, epalrestat, zenarestat, zopolrestat, minalrestat, fidarestat, CT-112), neurotrophic factors and increasing drugs thereof (e.g., NGF, NT-3, BDNF, neurotrophin production/secretion promoting agent described in WO01/14372 (e.g., 4-(4-chlorophenyl)-2-(2-methyl-1-imidazolyl)-5-[3-(2-methylphenoxy)propyl]oxazole)), nerve regeneration promoters (e.g., Y-128), PKC inhibitors (e.g., ruboxistaurin mesylate), AGE inhibitors (e.g., ALT946, pimagedine, N-phenacylthiazolium bromide (ALT766), ALT-711, EXO-226, pyridorin, pyridoxamine), active oxygen scavengers (e.g., thioctic acid), cerebral vasodilators (e.g., tiapuride, mexiletine), somatostatin receptor agonists (e.g., BIM23190), and apoptosis signal regulating kinase-1 (ASK-1) inhibitors.

Examples of the therapeutic agent for hyperlipidemia include HMG-CoA reductase inhibitors (e.g., pravastatin, simvastatin, lovastatin, atorvastatin, fluvastatin, pitavastatin, rosuvastatin or a salt thereof (e.g., sodium salt, calcium salt)), squalene synthase inhibitors (e.g., the compound described in WO 97/10224, for example, N-[[(3R,5S)-1-(3-acetoxy-2,2-dimethylpropyl)-7-chloro-5-(2,3-dimethoxyphenyl)-2-oxo-1,2,3,5-tetrahydro-4,1-benzoxazepin-3-yl]acetyl]piperidine-4-acetic acid), fibrate compounds (e.g., bezafibrate, clofibrate, simfibrate, clinofibrate), ACAT inhibitors (e.g., avasimibe, eflucimibe), anion exchange resins (e.g., colestyramine), probucol, nicotinic acid drugs (e.g., nicomol, niceritrol), ethyl icosapentate, phytosterol (e.g., soysterol, γ-oryzanol) and the like.

Examples of the antihypertensive agent include angiotensin converting enzyme inhibitors (e.g., captopril, enalapril, delapril), angiotensin II receptor antagonists (e.g., candesartan cilexetil, losartan, eprosartan, valsartan, telmisartan, irbesartan, tasosartan, 1-[[2'-(2,5-dihydro-5-oxo-4H-1,2,4-oxadiazol-3-yl)biphenyl-4-yl]methyl]-2-ethoxy-1H-benzimidazole-7-carboxylic acid), calcium antagonists (e.g., manidipine, nifedipine, amlodipine, efonidipine, nicardipine), potassium channel openers (e.g., levcromakalim, L-27152, AL 0671, NIP-121), clonidine and the like.

Examples of the antiobesitic agent include antiobestic agents acting on the central nervous system (e.g., dexfenfluramine, fenfluramine, phentermine, sibutramine, amfepramone, dexamphetamine, mazindol, phenylpropanolamine, clobenzorex; MCH receptor antagonists (e.g., SB-568849; SNAP-7941; compounds described in WO01/82925 and WO01/87834); neuropeptide Y antagonists (e.g., CP-422935); cannabinoid receptor antagonists (e.g., SR-141716, SR-147778); ghrelin antagonist), pancreatic lipase inhibitors (e.g., orlistat, cetilistat), β3 agonists (e.g., AJ-9677), anorectic peptides (e.g., leptin, CNTF (ciliary neurotrophic factor)), cholecystokinin agonists (e.g., lintitript, FPL-15849), feeding deterrents (e.g., P-57) and the like.

Examples of the diuretic include xanthine derivatives (e.g., theobromine sodium salicylate, theobromine calcium salicylate), thiazide preparations (e.g., ethiazide, cyclopenthiazide, trichloromethiazide, hydrochlorothiazide, hydroflumethiazide, benzylhydrochlorothiazide, penflutizide, polythiazide, methyclothiazide), antialdosterone preparations (e.g., spironolactone, triamterene), carbonic anhydrase inhibitors (e.g., acetazolamide), chlorobenzenesulfonamide agents (e.g., chlortalidone, mefruside, indapamide), azosemide, isosorbide, ethacrynic acid, piretanide, bumetanide, furosemide and the like.

Examples of the antithrombotic agent include heparins (e.g., heparin sodium, heparin calcium, dalteparin sodium), warfarins (e.g., warfarin potassium), anti-thrombin drugs (e.g., aragatroban), thrombolytic agents (e.g., urokinase, tisokinase, alteplase, nateplase, monteplase, pamiteplase), platelet aggregation inhibitors (e.g., ticlopidine hydrochloride, cilostazol, ethyl icosapentate, beraprost sodium, sarpogrelate hydrochloride) and the like.

Of the above-mentioned combination drugs, insulin preparations, α-glucosidase inhibitors (preferably voglibose, acarbose), biguanides (preferably buformin hydrochloride), sulfonylureas (preferably glimepiride) and the like are preferable.

When the solid preparation of the present invention and a concomitant drug are used in combination, the administration time of these is not limited, and the solid preparation of the present invention and the combination drug can be administered simultaneously to an administration subject, or may be administered in a staggered manner.

In addition, the solid preparation of the present invention and the concomitant drug may be administered as separate preparations to an administration subject, or the solid preparation of the present invention and the concomitant drug may be administered to an administration subject as a single preparation comprising the solid preparation of the present invention and the concomitant drug.

The dose of the concomitant drug can be appropriately determined based on the clinically employed dose of each drug. In addition, the mixing ratio of the solid preparation of the present invention and the concomitant drug can be appropriately determined according to the administration subject, administration route, target disease, condition, combination and the like. For example, when the administration subject is a human, the concomitant drug may be used in an amount of 0.01 to 100 parts by weight per 1 part by weight of the solid preparation of the present invention.

Use of the concomitant drug in this way provides superior effects such as 1) enhanced action of the solid preparation of the present invention or the concomitant drug (synergistic effect of the actions of the pharmaceutical agents), 2) reduced dose of the solid preparation of the present invention or the combination drug (effect of reduction of dose of pharmaceutical agents as compared to single drug administration), 3) reduced secondary action of the solid preparation of the present invention or the concomitant drug, and the like.

EXAMPLES

The present invention is explained in detail in the following by referring to Production Examples, Comparative Production Examples, and Experimental Examples, which are not to be construed as limitative, and can be modified without substantially departing from the spirit and scope of the present invention. As preparation additives (e.g., mannitol, hydroxypropylmethylcellulose, hydroxypropylcellulose, crospovidone, magnesium stearate, crystalline cellulose, polyvinylpyrrolidone, talc, titanium oxide, ferric oxide, polyethylene glycol) in the following Production Examples and Comparative Production Examples, those compatible to the Japanese Pharmacopoeia 15th Edition or Japanese Pharmaceutical Excipients 2003 were used.

Production Example 1

A mixture of benzoate (177.08 g) of compound (I), mannitol (262.5 g) and crystalline cellulose (31.25 g) was subjected to fluidized bed granulation (POWREX CORPORATION, model: LAB-1) while spraying an aqueous solution (292 g) of polyvinylpyrrolidone (29.18 g) to give granules containing compound (IA).

Separately, a mixture of metformin hydrochloride (463.0 g) and crystalline cellulose (11.11 g) was subjected to fluidized bed granulation (POWREX CORPORATION, model:

LAB-1) while spraying an aqueous solution (259 g) of polyvinylpyrrolidone (25.93 g) to give granules containing metformin hydrochloride.

The above-mentioned granules (9.6 g) containing compound (IA), the granules (432.2 g) containing metformin hydrochloride and crystalline cellulose (CEOLUS KG-802, 25.1 g), crospovidone (Kollidon CL-F, 24.63 g) and magnesium stearate (1.48 g) were mixed to give a powder mixture. The obtained powder mixture was tableted using a rotary tableting machine (KIKUSUI SEISAKUSYO LTD.) at a tableting pressure of 17.5 kN/punch (18.5 mm×10.0 mm oval shape) to give 1230 mg tablets.

Titanium oxide (3.76 g) and ferric oxide (0.043 g) were dispersed in purified water (216 g) to give dispersion liquid 1. Hydroxypropylcellulose (60.01 g), polyethylene glycol (6 g) and talc (2.21 g) were dissolved or dispersed in purified water (432 g) to give dispersion liquid 2. The obtained dispersion liquid 1 and dispersion liquid 2 were mixed to give a coating liquid. Using a coating machine (Freund Corporation, model: Hicoater mini), the coating liquid was sprayed on the tablets obtained above until the weight of each tablet increased by 36 mg to give coated tablets. Each coated tablet contains a benzoate (8.5 mg) of compound (I) and metformin hydrochloride (1000 mg).

Production Example 2

A mixture of benzoate (347.01 g) of compound (I), mannitol (1428.6 g) and crystalline cellulose (122.48 g) was subjected to fluidized bed granulation (POWREX CORPORATION, model: FD-3S) while spraying an aqueous solution (1020 g) of polyvinylpyrrolidone (102.06 g) to give granules containing compound (IA).

Separately, a mixture of metformin hydrochloride (1851.9 g) and crystalline cellulose (44.44 g) was subjected to fluidized bed granulation (POWREX CORPORATION, model: FD-3S) while spraying an aqueous solution (1037 g) of polyvinylpyrrolidone (103.7 g) to give granules containing metformin hydrochloride.

The above-mentioned granules (58.8 g) containing compound (IA), the granules (648 g) containing metformin hydrochloride and crystalline cellulose (CEOLUS KG-802, 39.6 g), crospovidone (Kollidon CL-F, 39.6 g) and magnesium stearate (2.4 g) were mixed to give a powder mixture. The obtained powder mixture was tableted using a rotary tableting machine (KIKUSUI SEISAKUSYO LTD.) at a tableting pressure of 11.2 kN/punch (16.3 mm×8.1 mm oval shape) to give 660 mg tablets.

Titanium oxide (9.65 g) and ferric oxide (0.1 g) were dispersed in purified water (210 g) to give dispersion liquid 1. Hydroxypropylcellulose (70 g) and talc (10.25 g) were dissolved or dispersed in purified water (600 g) to give dispersion liquid 2. The obtained dispersion liquid 1 and dispersion liquid 2 were mixed to give a coating liquid. Using a coating machine (Freund Corporation, model: Hicoater mini), the coating liquid was sprayed on the tablets obtained above until the weight of each tablet increased by 18 mg to give coated tablets. Each coated tablet contains a benzoate (8.5 mg) of compound (I) and metformin hydrochloride (500 mg).

Production Example 3

The compound (IA)-containing granules (117.7 g) obtained in Production Example 2, the metformin hydrochloride-containing granules (648 g) obtained in Production Example 2 and crystalline cellulose (CEOLUS KG-802, 43.1 g), crospovidone (Kollidon CL-F, 43.1 g) and magnesium stearate (2.65 g) were mixed to give a powder mixture. The obtained powder mixture was tableted using a rotary tableting machine (KIKUSUI SEISAKUSYO LTD.) at a tableting pressure of 13.5 kN/punch (16.3 mm×8.1 mm oval shape) to give 714 mg tablets.

Titanium oxide (9.65 g) and ferric oxide (0.1 g) were dispersed in purified water (210 g) to give dispersion liquid 1. Hydroxypropylcellulose (70 g) and talc (10.25 g) were dissolved or dispersed in purified water (600 g) to give dispersion liquid 2. The obtained dispersion liquid 1 and dispersion liquid 2 were mixed to give a coating liquid. Using a coating machine (Freund Corporation, model: Hicoater mini), the coating liquid was sprayed on the tablets obtained above until the weight of each tablet increased by 18 mg to give coated tablets. Each coated tablet contains a benzoate (17 mg) of compound (I) and metformin hydrochloride (500 mg).

Production Example 4

The compound (IA)-containing granules (49 g) obtained in Production Example 2, the metformin hydrochloride-containing granules (1080 g) obtained in Production Example 2 and crystalline cellulose (CEOLUS KG-802, 63.1 g), crospovidone (Kollidon CL-F, 63.1 g) and magnesium stearate (3.82 g) were mixed to give a powder mixture. The obtained powder mixture was tableted using a rotary tableting machine (KIKUSUI SEISAKUSYO LTD.) at a tableting pressure of 16.3 kN/punch (18.5 mm×10.0 mm oval shape) to give 1204 mg tablets.

Titanium oxide (9.65 g) and ferric oxide (0.1 g) were dispersed in purified water (210 g) to give dispersion liquid 1. Hydroxypropylcellulose (70 g) and talc (10.25 g) were dissolved or dispersed in purified water (600 g) to give dispersion liquid 2. The obtained dispersion liquid 1 and dispersion liquid 2 were mixed to give a coating liquid. Using a coating machine (Freund Corporation, model: Hicoater mini), the coating liquid was sprayed on the tablets obtained above until the weight of each tablet increased by 36 mg to give coated tablets. Each coated tablet contains a benzoate (8.1 mg) of compound (I) and metformin hydrochloride (950 mg).

Production Example 5

The compound (IA)-containing granules (98 g) obtained in Production Example 2, the metformin hydrochloride-containing granules (1080.2 g) obtained in Production Example 2 and crystalline cellulose (CEOLUS KG-802, 66 g), crospovidone (Kollidon CL-F, 66 g) and magnesium stearate (4.01 g) were mixed to give a powder mixture. The obtained powder mixture was tableted using a rotary tableting machine (KIKUSUI SEISAKUSYO LTD.) at a tableting pressure of 16.6 kN/punch (18.5 mm×10.0 mm oval shape) to give 1220 mg tablets.

Titanium oxide (9.65 g) and ferric oxide (0.1 g) were dispersed in purified water (210 g) to give dispersion liquid 1. Hydroxypropylcellulose (70 g) and talc (10.25 g) were dissolved or dispersed in purified water (600 g) to give dispersion liquid 2. The obtained dispersion liquid 1 and dispersion liquid 2 were mixed to give a coating liquid. Using a coating machine (Freund Corporation, model: Hicoater mini), the coating liquid was sprayed on the tablets obtained above until the weight of each tablet increased by 36 mg to give coated tablets. Each coated tablet contains a benzoate (15.8 mg) of compound (I) and metformin hydrochloride (930 mg).

Production Example 6

A mixture of benzoate (364.29 g) of compound (I), mannitol (1411.8 g) and crystalline cellulose (122.5 g) was subjected to fluidized bed granulation (POWREX CORPORATION, model: FD-3S) while spraying an aqueous solution (1020 g) of polyvinylpyrrolidone (102.1 g) to give granules containing compound (IA).

Separately, a mixture of metformin hydrochloride (1851.2 g) and crystalline cellulose (44.4 g) was subjected to fluidized bed granulation (POWREX CORPORATION, model: FD-3S) while spraying an aqueous solution (1037 g) of polyvinylpyrrolidone (103.8 g) to give granules containing metformin hydrochloride.

The weight ratio of each particle size was determined by sieving granules (about 50 g) using a 30 mesh (aperture 500 μm), 42 mesh (aperture 355 μm), 60 mesh (aperture 250 μm) and 100 mesh (aperture 150 μm) sieves, and measuring the weight of the granules remaining on each sieve and the granules that passed through a 100 mesh sieve.

The results of the measurement using about 50 g of granules containing compound (IA) were 30 mesh residue (0.1%), 42 mesh residue (0.1%), 60 mesh residue (0.5%), 100 mesh residue (30.1%) and 100 mesh passage (69.2%). That is, particles with not less than 250 μm was 0.7%, and particles with less than 150 μm was 69.2%.

The results of the measurement using about 50 g of granules containing metformin hydrochloride were 30 mesh residue (1.8%), 42 mesh residue (0.8%), 60 mesh residue (1.0%), 100 mesh residue (32.2%) and 100 mesh passage (64.2%). That is, particles with not less than 250 μm was 3.6%, and particles with less than 150 μm was 64.2%.

The above-mentioned granules (39.23 g) containing compound (IA), the granules (431.9 g) containing metformin hydrochloride and crystalline cellulose (CEOLUS KG-1000, 26.42 g), crospovidone (Kollidon CL-F, 26.41 g) and magnesium stearate (1.59 g) were mixed to give a powder mixture. The obtained powder mixture was tableted using a rotary tableting machine (KIKUSUI SEISAKUSYO LTD.) at a tableting pressure of kN/punch (14 mm×9 mm oval shape) to give 657 mg tablets.

Titanium oxide (9.69 g) and ferric oxide (0.1 g) were dispersed in purified water (209.8 g) to give dispersion liquid 1. Hydroxypropylcellulose (70.02 g) and talc (10.25 g) were dissolved or dispersed in purified water (600.2 g) to give dispersion liquid 2. The obtained dispersion liquid 1 and dispersion liquid 2 were mixed to give a coating liquid. Using a coating machine (Freund Corporation, model: Hicoater mini), the coating liquid was sprayed on the tablets obtained above until the weight of each tablet increased by 18 mg to give coated tablets. Each coated tablet contains a benzoate (8.5 mg) of compound (I) and metformin hydrochloride (500 mg).

Production Example 7

The compound (IA)-containing granules (78.39 g) obtained in Production Example 6, the metformin hydrochloride-containing granules (432 g) obtained in Production Example 6 and crystalline cellulose (CEOLUS KG-1000, 28.76 g), crospovidone (Kollidon CL-F, 28.73 g) and magnesium stearate (1.76 g) were mixed to give a powder mixture. The obtained powder mixture was tableted using a rotary tableting machine (KIKUSUI SEISAKUSYO LTD.) at a tableting pressure of 15 kN/punch (14 mm×9 mm oval shape) to give 712 mg tablets.

Titanium oxide (9.64 g) and ferric oxide (0.099 g) were dispersed in purified water (210.1 g) to give dispersion liquid 1. Hydroxypropylcellulose (70.45 g) and talc (10.25 g) were dissolved or dispersed in purified water (600.2 g) to give dispersion liquid 2. The obtained dispersion liquid 1 and dispersion liquid 2 were mixed to give a coating liquid. Using a coating machine (Freund Corporation, model: Hicoater mini), the coating liquid was sprayed on the tablets obtained above until the weight of each tablet increased by 18 mg to give coated tablets. Each coated tablet contains a benzoate (17 mg) of compound (I) and metformin hydrochloride (500 mg).

Production Example 8

The compound (IA)-containing granules (22.13 g) obtained in Production Example 6, the metformin hydrochloride-containing granules (485.9 g) obtained in Production Example 6 and crystalline cellulose (CEOLUS KG-1000, 28.39 g), crospovidone (Kollidon CL-F, 28.37 g) and magnesium stearate (1.71 g) were mixed to give a powder mixture. The obtained powder mixture was tableted using a rotary tableting machine (KIKUSUI SEISAKUSYO LTD.) at a tableting pressure of 20 kN/punch (18.5 mm×11.5 mm oval shape) to give 1259 mg tablets.

Titanium oxide (9.69 g) and ferric oxide (0.1 g) were dispersed in purified water (209.8 g) to give dispersion liquid 1. Hydroxypropylcellulose (70.02 g) and talc (10.25 g) were dissolved or dispersed in purified water (600.2 g) to give dispersion liquid 2. The obtained dispersion liquid 1 and dispersion liquid 2 were mixed to give a coating liquid. Using a coating machine (Freund Corporation, model: Hicoater mini), the coating liquid was sprayed on the tablets obtained above until the weight of each tablet increased by 36 mg to give coated tablets. Each coated tablet contains a benzoate (8.5 mg) of compound (I) and metformin hydrochloride (1000 mg).

Production Example 9

The compound (IA)-containing granules (44.12 g) obtained in Production Example 6, the metformin hydrochloride-containing granules (486 g) obtained in Production Example 6 and crystalline cellulose (CEOLUS KG-1000, 29.7 g), crospovidone (Kollidon CL-F, 29.71 g) and magnesium stearate (1.8 g) were mixed to give a powder mixture. The obtained powder mixture was tableted using a rotary tableting machine (KIKUSUI SEISAKUSYO LTD.) at a tableting pressure of 20 kN/punch (18.5 mm×11.5 mm oval shape) to give 1314 mg tablets.

Titanium oxide (9.64 g) and ferric oxide (0.099 g) were dispersed in purified water (210.1 g) to give dispersion liquid 1. Hydroxypropylmethylcellulose (70.45 g) and talc (10.25 g) were dissolved or dispersed in purified water (600.2 g) to give dispersion liquid 2. The obtained dispersion liquid 1 and dispersion liquid 2 were mixed to give a coating liquid. Using a coating machine (Freund Corporation, model: Hicoater mini), the coating liquid was sprayed on the tablets obtained above until the weight of each tablet increased by 36 mg to give coated tablets. Each coated tablet contains a benzoate (17 mg) of compound (I) and metformin hydrochloride (1000 mg).

Production Example 10

A mixture of metformin hydrochloride (1666 g) and crystalline cellulose (27.37 g) was subjected to fluidized bed granulation (POWREX CORPORATION, model: FD-3S) while spraying an aqueous solution (1000 g) of polyvinylpyrrolidone (100 g) to give granules containing metformin hydrochloride. The metformin hydrochloride-containing granules (1435.2 g), crystalline cellulose (80 g), crospovidone (80 g) and magnesium stearate (4.8 g) were mixed to give a powder mixture containing metformin hydrochloride. The obtained powder mixture was tableted using a rotary tableting machine (KIKUSUI SEISAKUSYO LTD.) at a tableting pressure of 16.5 kN/punch (18.5 mm×10 mm oval shape) to give 1200 mg metformin hydrochloride-containing tablets.

Hydroxypropylcellulose (21.61 g) and talc (2.4 g) were dissolved or dispersed in purified water (275.9 g) to give an intermediate layer coating liquid. Also, hydroxypropylcellulose (3.21 g), mannitol (68.3 g) and a benzoate (8.52 g) of compound (I) were dissolved in purified water (720 g) to give a compound (IA)-containing coating liquid. Titanium oxide (9.64 g) and ferric oxide (0.099 g) were dispersed in purified water (210 g) to give dispersion liquid 1. Hydroxypropylcellulose (70 g) and talc (10.25 g) were dissolved or dispersed in purified water (600 g) to give dispersion liquid 2. The obtained dispersion liquid 1 and dispersion liquid 2 were mixed to give a top layer coating liquid.

Using a coating machine (Freund Corporation, model: Hicoater mini), the intermediate layer coating liquid was spray-dried on the metformin hydrochloride-containing tablets until the weight of each tablet increased by 24 mg, then the compound (IA)-containing coating liquid was spray-dried thereon until the weight of each tablet increased by 80 mg, and then the top layer coating liquid was spray-dried thereon until the weight of each tablet increased by 36 mg to give coated tablets. Each coated tablet contained a benzoate (8.5 mg) of compound (I) and metformin hydrochloride (1000 mg).

Production Example 11

A mixture of benzoate (21.216 kg) of compound (I), mannitol (84 kg) and crystalline cellulose (7.2 kg) was subjected to fluidized bed granulation (Glatt, model: WSG120) while spraying an aqueous solution (60 kg) of polyvinylpyrrolidone (6 kg) and sieved by a granulating device (Quadro Engineering, model: Comil 194S) to give granules containing compound (IA).

Separately, a mixture of metformin hydrochloride (100 kg) and crystalline cellulose (2.4 kg) was subjected to fluidized bed granulation (Glatt, model: WSG120) while spraying an aqueous solution (28 kg) of polyvinylpyrrolidone (5.6 kg) and sieved by a granulating device (Quadro Engineering, model: Comil 194S). Two batches were produced on the above-mentioned production scale and mixed to give granules containing metformin hydrochloride.

The above-mentioned granules (19.345 kg) containing compound (IA), the granules (213.186 kg) containing metformin hydrochloride and crystalline cellulose (CEOLUS KG-1000, 13.028 kg), crospovidone (Kollidon CL-F, 13.028 kg) and magnesium stearate (0.79 kg) were mixed to give a powder mixture. The obtained powder mixture was tableted using a rotary tableting machine (KIKUSUI SEISAKUSYO LTD. model: PEGA1024) at a tableting pressure of 15 kN/punch (17.6 mm×8.4 mm oblong shape) to give 657 mg tablets.

Titanium oxide (1.235 kg) and red ferric oxide (12.8 g) were dispersed in purified water (26.88 kg) to give dispersion liquid 1. Hydroxypropylmethylcellulose (8.96 kg) and talc (1.312 kg) were dissolved or dispersed in purified water (76.8 kg) to give dispersion liquid 2. The obtained dispersion liquid 1 and dispersion liquid 2 were mixed to give a coating liquid. Using a coating machine (Freund Corporation, model: AQC-170FS), the coating liquid was sprayed on the tablets obtained above until the weight of each tablet increased by 18 mg to give coated tablets containing compound (I) (6.25 mg, free form) and metformin hydrochloride (500 mg) per tablet.

Production Example 12

The compound (IA)-containing granules (38.727 kg) obtained by production in the same manner as in Production Example 11, the metformin hydrochloride-containing granules (213.396 kg) obtained by production in the same manner as in Production Example 11, crystalline cellulose (CEOLUS KG-1000, 14.187 kg), crospovidone (Kollidon CL-F, 14.187 kg) and magnesium stearate (0.869 kg) were mixed to give a powder mixture. The obtained powder mixture was tableted using a rotary tableting machine (KIKUSUI SEISAKUSYO LTD. model: PEGA1024) at a tableting pressure of 14.8 kN/punch (17.6 mm×8.4 mm oblong shape) to give 712 mg tablets.

Titanium oxide (1.235 kg) and yellow ferric oxide (12.8 g) were dispersed in purified water (26.88 kg) to give dispersion liquid 1. Hydroxypropylmethylcellulose (8.96 kg) and talc (1.312 kg) were dissolved or dispersed in purified water (76.8 kg) to give dispersion liquid 2. The obtained dispersion liquid 1 and dispersion liquid 2 were mixed to give a coating liquid. Using a coating machine (Freund Corporation, model: AQC-170FS), the coating liquid was sprayed on the tablets obtained above until the weight of each tablet increased by 18 mg to give coated tablets containing compound (I) (12.5 mg, free form) and metformin hydrochloride (500 mg) per tablet.

Production Example 13

The compound (IA)-containing granules (9.618 kg) obtained by production in the same manner as in Production Example 11, the metformin hydrochloride-containing granules (211.98 kg) obtained by production in the same manner as in Production Example 11, crystalline cellulose (CEOLUS KG-1000, 12.385 kg), crospovidone (Kollidon CL-F, 12.385 kg) and magnesium stearate (0.746 kg) were mixed to give a powder mixture. The obtained powder mixture was tableted using a rotary tableting machine (KIKUSUI SEISAKUSYO LTD. model: PEGA1024) at a tableting pressure of 19.2 kN/punch (22 mm×10.5 mm oblong shape) to give 1259 mg tablets.

Titanium oxide (1.235 kg) and red ferric oxide (12.8 g) were dispersed in purified water (26.88 kg) to give dispersion liquid 1. Hydroxypropylmethylcellulose (8.96 kg) and talc (1.312 kg) were dissolved or dispersed in purified water (76.8 kg) to give dispersion liquid 2. The obtained dispersion liquid 1 and dispersion liquid 2 were mixed to give a coating liquid. Using a coating machine (Freund Corporation, model: AQC-170FS), the coating liquid was sprayed on the tablets obtained above until the weight of each tablet increased by 36 mg to give coated tablets containing compound (I) (6.25 mg, free form) and metformin hydrochloride (1000 mg) per tablet.

Production Example 14

The compound (IA)-containing granules (19.311 kg) obtained by production in the same manner as in Production Example 11, the metformin hydrochloride-containing granules (212.814 kg) obtained by production in the same manner as in Production Example 11, crystalline cellulose (CEOLUS KG-1000, 13.005 kg), crospovidone (Kollidon CL-F, 13.006 kg) and magnesium stearate (0.788 kg) were mixed to give a powder mixture. The obtained powder mixture was tableted using a rotary tableting machine (KIKUSUI SEISAKUSYO LTD. model: PEGA1024) at a tabletting pressure of 24.4 kN/punch (22 mm×10.5 mm oblong shape) to give 1314 mg tablets.

Titanium oxide (1.235 kg) and yellow ferric oxide (12.8 g) were dispersed in purified water (26.88 kg) to give dispersion liquid 1. Hydroxypropylmethylcellulose (8.96 kg) and talc (1.312 kg) were dissolved or dispersed in purified water (76.8 kg) to give dispersion liquid 2. The obtained dispersion liquid 1 and dispersion liquid 2 were mixed to give a coating liquid. Using a coating machine (Freund Corporation, model: AQC-170FS), the coating liquid was sprayed on the tablets obtained above until the weight of each tablet increased by 36 mg to give coated tablets containing compound (I) (12.5 mg, free form) and metformin hydrochloride (1000 mg) per tablet.

Production Example 15

The compound (IA)-containing granules (980.04 mg) obtained by production in the same manner as in Production Example 11, crystalline cellulose (60.16 mg) (CEOLUS KG-1000), crospovidone (59.95 mg) (Kollidon CL-F) and magnesium stearate (5.06 mg) were mixed to give a powder mixture containing compound (IA). The metformin hydrochloride-containing granules (5.40162 g) obtained by production in the same manner as in Production Example 11, crystalline cellulose (CEOLUS KG-1000, 299.01 mg), crospovidone (Kollidon CL-F, 300.1 mg) and magnesium stearate (16.07 mg) were mixed to give a powder mixture containing metformin hydrochloride. Using a desktop portable tabletting machine (ICHIHASHI SEIKI CO., LTD., HANDTAB200), the metformin hydrochloride-containing powder mixture (601.38 mg) was tabletted firstly at a tabletting pressure of 3 kN/punch (17.6 mm×8.4 mm oblong shape) to form the first layer, and then the obtained compound (IA)-containing powder mixture (109.72 mg) was added and the mixture was tabletted at a tabletting pressure of 14 kN/punch to give a bilayer tablet. The bilayer tablet contained a benzoate (17 mg) of compound (I) and metformin hydrochloride (500 mg) per tablet.

Production Example 16

Using a desktop portable tabletting machine tabletting machine (ICHIHASHI SEIKI CO., LTD., HANDTAB200), the metformin hydrochloride-containing powder mixture (301.19 mg) obtained in Production Example 15 was tabletted at a tabletting pressure of 3 kN/punch (17.6 mm×8.4 mm oblong shape) to form the first layer, then the compound (IA)-containing powder mixture (109.34 mg) obtained in Production Example 15 was added and the mixture was tabletted at a tabletting pressure of 4 kN/punch to form the second layer, and the metformin hydrochloride-containing powder mixture (301.73 mg) obtained in Production Example 15 was further added and the mixture was tabletted at a tabletting pressure of 14 kN/punch to give a three-layer tablet. The three-layer tablet contained a benzoate (17 mg) of compound (I) and metformin hydrochloride (500 mg) per tablet.

Production Example 17

Using a desktop portable tabletting machine tabletting machine (ICHIHASHI SEIKI CO., LTD., HANDTAB200), the compound (IA)-containing powder mixture (109.2 mg) obtained in Production Example 15 was tabletted at a tabletting pressure of 5 kN/punch (7 mm diameter round shape) to give an inner core tablet containing compound (IA). Then the inner core tablet containing compound (IA) was placed at the center of the metformin hydrochloride-containing powder mixture (602.83 mg) obtained in Production Example 15 and tabletted at a tabletting pressure of 14 kN/punch (17.6 mm×8.4 mm oblong shape) to give a press-coated tablet. The press-coated tablet contained a benzoate (17 mg) of compound (I) and metformin hydrochloride (500 mg) per tablet.

Production Example 18

Firstly, crystalline cellulose (CEOLUS KG-1000, 329.79 mg) and crospovidone (Kollidon CL-F, 331 mg) were mixed to give a powder mixture for an intermediate layer. Using a desktop portable tabletting machine tabletting machine (ICHIHASHI SEIKI CO., LTD., HANDTAB200), the metformin hydrochloride-containing powder mixture (601.07 mg) obtained in Production Example 15 was tabletted at a tabletting pressure of 3 kN/punch (17.6 mm×8.4 mm oblong shape) to form the first layer, then the powder mixture (65.84 mg) for an intermediate layer was added and the mixture was tabletted at a tabletting pressure of 3 kN/punch to form the second layer, and the compound (IA)-containing powder mixture (110.47 mg) obtained in Production Example 15 was further added and the mixture was tabletted at a tabletting pressure of 14 kN/punch to give a three-layer tablet. The three-layer tablet contained a benzoate (17 mg) of compound (I) and metformin hydrochloride (500 mg) per tablet.

Production Example 19

Using a desktop portable tabletting machine tabletting machine (ICHIHASHI SEIKI CO., LTD., HANDTAB200), the metformin hydrochloride-containing powder mixture (301.13 mg) obtained in Production Example 15 was tabletted at a tabletting pressure of 3 kN/punch (17.6 mm×8.4 mm oblong shape) to form the first layer, then the powder mixture (33.35 mg) for an intermediate layer obtained in Production Example 18 was added and the mixture was tabletted at a tabletting pressure of 3 kN/punch to form the second layer, the compound (IA)-containing powder mixture (109.98 mg) obtained in Production Example 15 was further added and the mixture was tabletted at a tabletting pressure of 3 kN/punch to form the third layer, the powder mixture (32.62 mg) for an intermediate layer obtained in Production Example 18 was added and the mixture was tabletted at a tabletting pressure of 3 kN/punch to form the fourth layer, and then the metformin hydrochloride-containing powder mixture (300.62 mg) obtained in Production Example 15 was added and the mixture was tabletted at a tabletting pressure of 14 kN/punch to give a five-layer tablet. The five-layer tablet contained a benzoate (17 mg) of compound (I) and metformin hydrochloride (500 mg) per tablet.

Comparative Production Example 1

A mixture of a benzoate (8.94 g) of compound (I), metformin hydrochloride (999.7 g) and crystalline cellulose (43.17 g) was subjected to fluidized bed granulation (POWREX CORPORATION, model: FD-3S) while spraying an aqueous solution (610 g) of polyvinylpyrrolidone (61 g) to give granules containing compound (IA)/metformin hydrochloride. The granules (1020.5 g), crystalline cellulose (55.95 g), Ac-Di-Sol (39.19 g) and magnesium stearate (3.36 g) were mixed to give a powder mixture. The obtained powder mixture was tabletted using a rotary tabletting machine (KIKUSUI SEISAKUSYO LTD.) at a tabletting pressure of 26 kN/punch (18.5 mm×10 mm oval shape) to give 1220 mg tablets.

Titanium oxide (4 g) and ferric oxide (0.4 g) were dispersed in purified water (240.7 g) to give dispersion liquid 1. Hydroxypropylmethylcellulose2910 (59.7 g), polyethylene glycol (12.1 g) and talc (4 g) were dissolved or dispersed in purified water (480.3 g) to give dispersion liquid 2. The obtained dispersion liquid 1 and dispersion liquid 2 were mixed to give a coating liquid. Using a coating machine (Freund Corporation, model: Hicoater mini), the coating liquid was sprayed on the tablets obtained above until the weight of each tablet increased by 40 mg to give coated tablets. Each coated tablet contains a benzoate (8.5 mg) of compound (I) and metformin hydrochloride (1000 mg).

Experimental Example 1

The tablets of Production Examples 1-5 and Production Example 10, and the tablet of Comparative Production Example 1 were placed in glass containers and subjected to a preservation stability test under the preservation conditions described in Tables 1-7. The amounts of related substances RS1-6 after a given preservation period are shown in Tables 1-7. In the Tables, W means week, M means month and RT means relative elution time. The amounts of related substances were measured by high performance liquid chromatography analysis under the following conditions. In the Tables, the amounts of related substances are shown by the peak area ratio defined above when the peak area corresponding to the assumed content of compound (I) as defined above is 100. In the Experimental Examples, the assumed content of compound (I) in the preparations of Production Examples 1, 2, 4, and 10 as well as Comparative Production Example 1 is 6.25 mg and that in the preparations of Production Examples 3 and 5 is 12.5 mg. From the results, it is clear that the solid preparation of the present invention is superior in the stability.

[Preparation of Sample for High Performance Liquid Chromatography]

Five tablets were precisely weighed and placed in a 500 mL measuring flask. About 400 mL of 0.1N HCl was added and, after shaking for 30 min, the mixture was measured up with 1N HCl. After thorough mixing, a part of the solution (about 10 mL) was placed in a glass tube and centrifuged (3000 rpm, 5 min). The supernatant was filtered through a 0.45 μm filter (GHP Acrodisc 25 mm 0.45 μm, Japan Pall Corporation) to give a sample for HPLC.

[Conditions of High Performance Liquid Chromatography Analysis]

(1) column: Zorbax SB-CN, 5 μm, inner diameter 4.6 mm×25 cm
   (manufactured by Agilent)
(2) mobile phase:
   mobile phase A: purified water/acetonitrile/trifluoroacetic acid=1900/100/1 (volume ratio)
   mobile phase B: purified water/acetonitrile/trifluoroacetic acid=100/1900/1 (volume ratio)
(3) elution gradient program:
   from 0 min to 30 min: 99/1 (mobile phase A/mobile phase B) to 75/25 (mobile phase A/mobile phase B)
   from 30 min to 50 min: 75/25 (mobile phase A/mobile phase B) to 10/90 (mobile phase A/mobile phase B)
   from 50 min to 51 min: 10/90 (mobile phase A/mobile phase B) to 99/1 (mobile phase A/mobile phase B)
   from 51 min to 60 min: 99/1 (mobile phase A/mobile phase B) constant)
(4) flow rate: 1 ml/min
(5) detector: UV 278 nm
(6) sample temperature: about 3° C.-about 10° C.
(7) column temperature: about 20° C.-about 30° C.

TABLE 1

| Production Example 1 | | RS-1 RT0.60 | RS-2 RT1.08 | RS-3 RT1.3 | RS-4 RT1.49 | RS-5 RT1.52 | RS-6 RT1.62 | total |
|---|---|---|---|---|---|---|---|---|
| Initial | | <0.05 | <0.05 | 0.060 | <0.05 | 0.068 | <0.05 | 0.128 |
| 40° C., 22% RH opened | 1M | <0.05 | <0.05 | <0.05 | <0.05 | <0.05 | 0.072 | 0.072 |
| 40° C., 33% RH opened | 1M | <0.05 | <0.05 | 0.063 | <0.05 | <0.05 | 0.095 | 0.158 |
| 40° C., 44% RH opened | 1M | <0.05 | <0.05 | <0.05 | <0.05 | <0.05 | 0.051 | 0.051 |
| 40° C., 57% RH opened | 1M | 0.050 | <0.05 | <0.05 | 0.051 | <0.05 | 0.076 | 0.177 |

TABLE 2

| Production Example 2 | | RS-1 RT0.60 | RS-2 RT1.08 | RS-3 RT1.3 | RS-4 RT1.49 | RS-5 RT1.52 | RS-6 RT1.62 | total |
|---|---|---|---|---|---|---|---|---|
| Initial | | <0.05 | <0.05 | <0.05 | <0.05 | <0.05 | <0.05 | 0.000 |
| 40° C., 33% RH opened | 1M | <0.05 | <0.05 | <0.05 | <0.05 | <0.05 | <0.05 | 0.000 |
| 40° C., 44% RH opened | 1M | <0.05 | <0.05 | <0.05 | <0.05 | <0.05 | <0.05 | 0.000 |
| 40° C., 57% RH opened | 1M | <0.05 | <0.05 | <0.05 | <0.05 | 0.059 | 0.062 | 0.121 |

TABLE 3

| Production Example 3 | | RS-1 RT0.60 | RS-2 RT1.08 | RS-3 RT1.3 | RS-4 RT1.49 | RS-5 RT1.52 | RS-6 RT1.62 | total |
|---|---|---|---|---|---|---|---|---|
| Initial | | <0.05 | <0.05 | <0.05 | <0.05 | <0.05 | 0.053 | 0.053 |
| 40° C., 33% RH opened | 1M | <0.05 | <0.05 | <0.05 | <0.05 | <0.05 | <0.05 | 0.000 |

TABLE 3-continued

| Production Example 3 | | RS-1 RT0.60 | RS-2 RT1.08 | RS-3 RT1.3 | RS-4 RT1.49 | RS-5 RT1.52 | RS-6 RT1.62 | total |
|---|---|---|---|---|---|---|---|---|
| 40° C., 44% RH opened | 1M | <0.05 | <0.05 | <0.05 | <0.05 | <0.05 | <0.05 | 0.000 |
| 40° C., 57% RH opened | 1M | <0.05 | <0.05 | <0.05 | <0.05 | <0.05 | <0.05 | 0.000 |

TABLE 4

| Production Example 4 | | RS-1 RT0.60 | RS-2 RT1.08 | RS-3 RT1.3 | RS-4 RT1.49 | RS-5 RT1.52 | RS-6 RT1.62 | total |
|---|---|---|---|---|---|---|---|---|
| Initial | | <0.05 | <0.05 | <0.05 | <0.05 | <0.05 | <0.05 | 0.000 |
| 40° C. 33% RH opened | 1M | <0.05 | <0.05 | <0.05 | <0.05 | <0.05 | 0.054 | 0.054 |
| 40° C. 44% RH opened | 1M | <0.05 | <0.05 | <0.05 | <0.05 | <0.05 | 0.059 | 0.059 |
| 40° C. 57% RH opened | 1M | 0.053 | <0.05 | <0.05 | <0.05 | <0.05 | 0.079 | 0.132 |

TABLE 5

| Production Example 5 | | RS-1 RT0.60 | RS-2 RT1.08 | RS-3 RT1.3 | RS-4 RT1.49 | RS-5 RT1.52 | RS-6 RT1.62 | total |
|---|---|---|---|---|---|---|---|---|
| Initial | | <0.05 | <0.05 | <0.05 | <0.05 | <0.05 | <0.05 | 0.000 |
| 40° C. 33% RH opened | 1M | <0.05 | <0.05 | <0.05 | <0.05 | <0.05 | <0.05 | 0.000 |
| 40° C. 44% RH opened | 1M | <0.05 | <0.05 | <0.05 | <0.05 | <0.05 | <0.05 | 0.000 |
| 40° C. 57% RH opened | 1M | <0.05 | <0.05 | <0.05 | <0.05 | <0.05 | 0.057 | 0.057 |

TABLE 6

| Production Example 10 | | RS-1 RT0.60 | RS-2 RT1.08 | RS-3 RT1.3 | RS-4 RT1.49 | RS-5 RT1.52 | RS-6 RT1.62 | total |
|---|---|---|---|---|---|---|---|---|
| Initial | | <0.05 | <0.05 | <0.05 | <0.05 | <0.05 | 0.061 | 0.061 |
| 40° C. 33% RH opened | 1M | 0.066 | <0.05 | <0.05 | <0.05 | <0.05 | 0.135 | 0.201 |
| 40° C. 44% RH opened | 1M | 0.069 | <0.05 | <0.05 | <0.05 | <0.05 | 0.132 | 0.201 |
| 40° C. 57% RH opened | 1M | 0.060 | <0.05 | <0.05 | <0.05 | <0.05 | 0.142 | 0.202 |

TABLE 7

| Comparative Production Example 1 | | RS-1 RT0.60 | RS-2 RT1.08 | RS-3 RT1.3 | RS-4 RT1.49 | RS-5 RT1.52 | RS-6 RT1.62 | total |
|---|---|---|---|---|---|---|---|---|
| initial | | <0.05 | <0.05 | <0.05 | <0.05 | <0.05 | <0.05 | 0.000 |
| 40° C., 33% RH opened | 1M | <0.05 | 0.295 | 0.686 | <0.05 | <0.05 | 0.145 | 1.126 |
| 40° C., 44% RH opened | 1M | <0.05 | 0.136 | 0.350 | <0.05 | <0.05 | 0.142 | 0.627 |
| 40° C., 57% RH opened | 1M | <0.05 | <0.05 | <0.05 | <0.05 | <0.05 | 0.149 | 0.149 |

Experimental Example 2

The tablets of Production Examples 11-14 and a desiccant were placed in polypropylene containers and subjected to a preservation stability test under the preservation conditions described in Tables 8-11. The amounts of related substances RS1-6 after a given preservation period are shown in Tables 8-11. In the Tables, M means month. The amounts of related substances were measured by high performance liquid chromatography analysis under the above conditions. In the Tables, the amounts of related substances are shown by the peak area ratio defined above when the peak area corresponding to the assumed content of compound (I) as defined above is 100. In all tablets, the amount of each related substance produced under severe conditions in the polypropylene container for 2 months was not more than 0.5%. From the results, it is clear that the solid preparation of the present invention is superior in the stability.

TABLE 8

| Production Example 11 | | RS-1 RT0.60 | RS-2 RT1.08 | RS-3 RT1.3 | RS-4 RT1.49 | RS-5 RT1.52 | RS-6 RT1.62 | total |
|---|---|---|---|---|---|---|---|---|
| initial | | <0.05 | <0.05 | <0.05 | <0.05 | <0.05 | <0.05 | 0.000 |
| 40° C., 75% RH tightly sealed 2M | 14 tablets | <0.05 | <0.05 | <0.05 | <0.05 | <0.05 | 0.089 | 0.089 |
| | 60 tablets | <0.05 | <0.05 | <0.05 | <0.05 | <0.05 | 0.092 | 0.092 |
| | 180 tablets | <0.05 | <0.05 | <0.05 | <0.05 | <0.05 | 0.092 | 0.092 |
| | 500 tablets | <0.05 | <0.05 | <0.05 | <0.05 | <0.05 | 0.093 | 0.093 |

TABLE 9

| Production Example 12 | | RS-1 RT0.60 | RS-2 RT1.08 | RS-3 RT1.3 | RS-4 RT1.49 | RS-5 RT1.52 | RS-6 RT1.62 | total |
|---|---|---|---|---|---|---|---|---|
| initial | | <0.05 | <0.05 | <0.05 | <0.05 | <0.05 | <0.05 | 0.000 |
| 40° C. 75% RH tightly sealed 2M | 14 tablets | <0.05 | <0.05 | <0.05 | <0.05 | <0.05 | 0.073 | 0.073 |
| | 60 tablets | <0.05 | <0.05 | <0.05 | <0.05 | <0.05 | 0.077 | 0.077 |
| | 180 tablets | <0.05 | <0.05 | <0.05 | <0.05 | <0.05 | 0.077 | 0.077 |
| | 500 tablets | <0.05 | <0.05 | <0.05 | <0.05 | <0.05 | 0.074 | 0.074 |

TABLE 10

| Production Example 13 | | RS-1 RT0.60 | RS-2 RT1.08 | RS-3 RT1.3 | RS-4 RT1.49 | RS-5 RT1.52 | RS-6 RT1.62 | total |
|---|---|---|---|---|---|---|---|---|
| initial | | <0.05 | <0.05 | <0.05 | <0.05 | <0.05 | <0.05 | 0.000 |
| 40° C. 75% RH tightly sealed 2M | 14 tablets | <0.05 | 0.061 | 0.059 | <0.05 | <0.05 | 0.110 | 0.230 |
| | 60 tablets | <0.05 | 0.056 | 0.053 | <0.05 | <0.05 | 0.109 | 0.218 |
| | 180 tablets | <0.05 | 0.056 | 0.056 | <0.05 | <0.05 | 0.116 | 0.228 |
| | 500 tablets | <0.05 | 0.053 | 0.053 | <0.05 | 0.050 | 0.114 | 0.270 |

TABLE 11

| Production Example 14 | | RS-1 RT0.60 | RS-2 RT1.08 | RS-3 RT1.3 | RS-4 RT1.49 | RS-5 RT1.52 | RS-6 RT1.62 | total |
|---|---|---|---|---|---|---|---|---|
| initial | | <0.05 | <0.05 | <0.05 | <0.05 | <0.05 | <0.05 | 0.000 |
| 40° C., 75% RH tightly sealed 2M | 14 tablets | <0.05 | <0.05 | <0.05 | <0.05 | <0.05 | <0.05 | 0.000 |
| | 60 tablets | <0.05 | <0.05 | <0.05 | <0.05 | <0.05 | 0.090 | 0.090 |
| | 180 tablets | <0.05 | <0.05 | <0.05 | <0.05 | <0.05 | 0.092 | 0.092 |
| | 500 tablets | <0.05 | <0.05 | <0.05 | <0.05 | <0.05 | 0.094 | 0.094 |

Experimental Example 3

Figure 2:
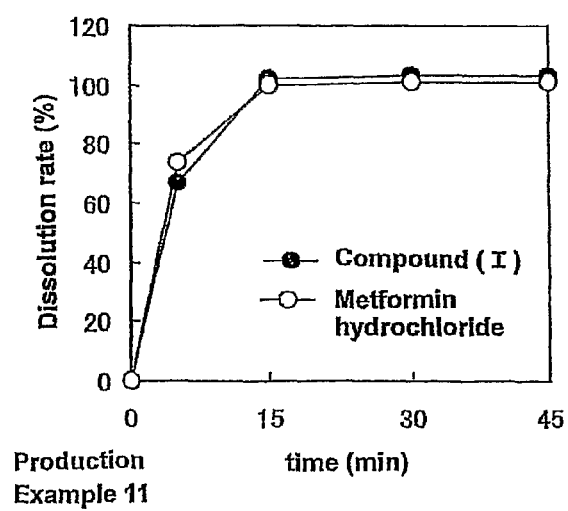
FIG. 2 is a graph showing the dissolution rate of Production Example 11.

The dissolution property of compound (I) and metformin hydrochloride from the preparations produced in Production Examples 11-14 was confirmed by the evaluation by the following test method. The apparatus of the Paddle Method (paddle rate: 50 rpm) from among the dissolution test methods described in the Japanese Pharmacopoeia Fifteenth Edition was used and a 0.01N aqueous hydrochloric acid solution (900 mL) warmed to 37° C. was used as an eluent. Samples were taken at 5 min, 15 min, 30 min and 45 min from the start of the dissolution, and the dissolution amounts of compound (I) and metformin hydrochloride were analyzed by high performance liquid chromatography. The results in percentage are shown in FIG. 2. All tablets showed rapid dissolution.

Experimental Example 4

The tablets of Production Example 8 and Comparative Production Example 1 were placed in glass containers and subjected to a stability test under the preservation conditions described in Table 12 and Table 13. The content of compound (I) and the amounts of related substances RS1-6 after a given preservation period are shown in Table 12 and Table 13. In the Tables, M means month. The content of compound (I) was measured by high performance liquid chromatography under the following analysis conditions, and calculated with the content before preservation as 100. The amount of related substances was measured under the same conditions as in the above-mentioned Experimental Example 1 and calculated. From the results, it is clear that the solid preparation of the present invention is superior in the stability as compared to Comparative Production Examples.

[Preparation of Sample for High Performance Liquid Chromatography]

Five tablets were precisely weighed and placed in a 500 mL measuring flask. About 400 mL of 0.1N HCl was added and, after shaking for 30 min, the mixture was measured up with 0.1N HCl. After thorough mixing, a part of the solution (about 10 mL) was placed in a glass tube and centrifuged (3000 rpm, 5 min). The supernatant was passed through a 0.45 μm filter (GHP Acrodisc 25 mm 0.45 μm, Japan Pall Corporation). The filtrate was diluted 10-fold with 0.1N HCl to give a sample for content measurement.

[Conditions of High Performance Liquid Chromatography Analysis]
(1) column: YMC Pack Pro C8 AS-212, 5 μm, inner diameter 6.0 mm×15 cm
(2) mobile phase: 0.025 mol/L SDS in 0.05 mol/L dihydrogen ammonium phosphate/acetonitrile=1/1 (volume ratio)
(3) flow rate: 1 ml/min
(5) detector: UV 255 nm
(6) sample temperature: about 3° C.-about 10° C.
(7) column temperature: about 20° C.-about 30° C.

TABLE 12

| Production Example 8 | | content % of initial | Related substances of compound I | | | | | | |
|---|---|---|---|---|---|---|---|---|---|
| | | | RS-1 RT0.60 | RS-2 RT1.08 | RS-3 RT1.3 | RS-4 RT1.49 | RS-5 RT1.52 | RS-6 RT1.62 | total |
| Initial | | 100.0 | 0.065 | <0.05 | <0.05 | <0.05 | <0.05 | <0.05 | 0.065 |
| 40° C. 33% RH | 1M | 98.1 | 0.053 | <0.05 | <0.05 | <0.05 | <0.05 | <0.05 | 0.053 |
| opened | 4M | 100.0 | 0.057 | 0.092 | 0.052 | 0.077 | <0.05 | <0.05 | 0.278 |
| 40° C. 44% RH | 1M | 98.0 | <0.05 | <0.05 | <0.05 | <0.05 | <0.05 | <0.05 | 0.000 |
| opened | 4M | 97.8 | 0.061 | <0.05 | <0.05 | 0.100 | <0.05 | 0.094 | 0.255 |

TABLE 13

| Comparative Production Example 1 | | content % of initial | Related substances of compound | | | | | | |
|---|---|---|---|---|---|---|---|---|---|
| | | | RS-1 RT0.60 | RS-2 RT1.08 | RS-3 RT1.3 | RS-4 RT1.49 | RS-5 RT1.52 | RS-6 RT1.62 | total |
| initial | | 100.0 | <0.05 | <0.05 | <0.05 | <0.05 | <0.05 | <0.05 | 0.000 |
| 40° C. 33% RH | 1M | 98.0 | <0.05 | 0.295 | 0.686 | <0.05 | <0.05 | 0.145 | 1.126 |
| opened | 2M | 95.4 | 0.060 | 0.598 | 1.072 | <0.05 | <0.05 | 0.219 | 1.949 |
| 40° C. 44% RH | 1M | 95.7 | <0.05 | 0.136 | 0.350 | <0.05 | <0.05 | 0.142 | 0.627 |
| opened | 2M | 96.7 | 0.061 | 0.276 | 0.455 | <0.05 | <0.05 | 0.210 | 1.002 |

INDUSTRIAL APPLICABILITY

The solid preparation of the present invention is useful as a therapeutic drug for diabetes and the like, and is superior in the preservation stability and the dissolution property of compound (I), a salt thereof and metformin hydrochloride.

This application is based on a patent application No. 2007-188574 filed in Japan (filing date: Jul. 19, 2007), the contents of which are incorporated in full herein by this reference.

The invention claimed is:

1. A solid preparation comprising the following first part and second part;
   the first part comprising 2-[[6-[(3R)-3-amino-1-piperidinyl]-3,4-dihydro-3-methyl-2,4-dioxo-1(2H)-pyrimidinyl]methyl]benzonitrile or a salt thereof and 0-3 parts by weight of metformin hydrochloride, relative to 100 parts by weight of the total weight of the first part; and
   the second part comprising metformin hydrochloride and 0-0.5 parts by weight of 2-[[6-[(3R)-3-amino-1-piperidinyl]-3,4-dihydro-3-methyl-2,4-dioxo-1(2H)-pyrimidinyl]methyl]benzonitrile or a salt thereof, relative to 100 parts by weight of the total weight of the second part;
   wherein the first part is physically separated from the second part.

2. The solid preparation of claim 1, further comprising an additive.

3. The solid preparation of claim 2, comprising about 0.5-200 mg of 2-[[6-[(3R)-3-amino-1-piperidinyl]-3,4-dihydro- 3-methyl-2,4-dioxo-1(2H)-pyrimidinyl]methyl]benzonitrile or a salt thereof, and about 0.1-about 2 g of metformin hydrochloride.

4. The solid preparation of claim 2, wherein the first part has an average particle size of not less than about 75 µm, and the second part has an average particle size of not less than about 75 µm.

5. The solid preparation of claim 2, wherein 2-[[6-[(3R)-3-amino-1-piperidinyl]-3,4-dihydro-3-methyl-2,4-dioxo-1 (2H)-pyrimidinyl]methyl]benzonitrile or a salt thereof is a benzoate of 2-[[6-[(3R)-3-amino-1-piperidinyl]-3,4-dihydro-3-methyl-2,4-dioxo-1(2H)-pyrimidinyl]methyl]benzonitrile.

6. The solid preparation of claim 2, which is a tablet.

7. The solid preparation of claim 2, wherein the first part and the second part are granules or tablets.

8. The solid preparation of claim 7, which is a capsule comprising said granule or said tablet.

9. The solid preparation of claim 2, wherein the weight ratio of 2-[[6-[(3R)-3-amino-1-piperidinyl]-3,4-dihydro-3-methyl-2,4-dioxo-1(2H)-pyrimidinyl]methyl]benzonitrile or a salt thereof contained in the first part and metformin hydrochloride contained in the second part is 1:5-1:400.

10. The solid preparation of claim 2, wherein the additive is a cellulose.

11. The solid preparation of claim 1, which is obtained by compression molding of a mixture of the following first granule and second granule:
the first granule comprising 2-[[6-[(3R)-3-amino-1-piperidinyl]-3,4-dihydro-3-methyl-2,4-dioxo-1(2H)-pyrimidinyl]methyl]benzonitrile or a salt thereof and 0-3 parts by weight of metformin hydrochloride, relative to 100 parts by weight of the total weight of the first granule; and
the second granule comprising metformin hydrochloride and 0-0.5 parts by weight of 2-[[6-[(3R)-3-amino-1-piperidinyl]-3,4-dihydro-3-methyl-2,4-dioxo-1(2H)-pyrimidinyl]methyl]benzonitrile or a salt thereof, relative to 100 parts by weight of the total weight of the second granule.

12. The solid preparation of claim 11, wherein
the proportion of the content of the first granule with a particle size of less than 150 µm relative to the total amount of the first granule is not less than about 20 wt %,
the proportion of the content of the first granule with a particle size of not less than 250 µm relative to the total amount of the first granule is not more than about 50 wt %,
the proportion of the content of the second granule with a particle size of less than 150 µm relative to the total amount of the second granule is not less than about 20 wt %, and
the proportion of the content of the second granule with a particle size of not less than 250 µm relative to the total amount of the second granule is not more than about 50 wt %.

13. The solid preparation of claim 11, wherein the weight ratio of 2-[[6-[(3R)-3-amino-1-piperidinyl]-3,4-dihydro-3-methyl-2,4-dioxo-1(2H)-pyrimidinyl]methyl]benzonitrile or a salt thereof contained in the first granule and metformin hydrochloride contained in the second granule is 1:5-1:400.

14. The solid preparation of claim 1,
wherein the first part is the following layer and the second part is the following core:
the core comprising metformin hydrochloride and 0-0.5 parts by weight of 2-[[6-[(3R)-3-amino-1-piperidinyl]-3,4-dihydro-3-methyl-2,4-dioxo-1(2H)-pyrimidinyl]methyl]benzonitrile or a salt thereof, relative to 100 parts by weight of the total weight of the core;
the layer comprising 2-[[6-[(3R)-3-amino-1-piperidinyl]-3,4-dihydro-3-methyl-2,4-dioxo-1(2H)-pyrimidinyl]methyl]benzonitrile or a salt thereof and 0-3 parts by weight of metformin hydrochloride, relative to 100 parts by weight of the total weight of the layer, or
wherein the first part is the following core and the second part is the following layer:
the core comprising 2-[[6-[(3R)-3-amino-1-piperidinyl]-3,4-dihydro-3-methyl-2,4-dioxo-1-(2H)-pyrimidinyl]methyl]benzonitrile or a salt thereof and 0-3 parts by weight of metformin hydrochloride, relative to 100 parts by weight of the total weight of the core;
the layer comprising metformin hydrochloride and 0-0.5 parts by weight of 2-[[6-[(3R)-3-amino-1-piperidinyl]-3,4-dihydro-3-methyl-2,4-dioxo-1(2H)-pyrimidinyl]methyl]benzonitrile or a salt thereof, relative to 100 parts by weight of the total weight of the layer.

15. The solid preparation of claim 14, further comprising an intermediate layer between said core and said layer.

16. The solid preparation of claim 14, wherein said layer is formed by spray coating.

17. The solid preparation of claim 14, wherein said layer is formed by compression.

18. The solid preparation of claim 1, wherein the first part is the following first layer and the second part is the following second layer:
the first layer comprising 2-[[6-[(3R)-3-amino-1-piperidinyl]-3,4-dihydro-3-methyl-2,4-dioxo-1(2H)-pyrimidinyl]methyl]benzonitrile or a salt thereof and 0-3 parts by weight of metformin hydrochloride, relative to 100 parts by weight of the total weight of the first layer; and
the second layer comprising metformin hydrochloride and 0-0.5 parts by weigh of 2-[[6-[(3R)-3-amino-1-piperidinyl]-3,4-dihydro-3-methyl-2,4-dioxo-1(2H)-pyrimidinyl]methyl]benzonitrile or a salt thereof, relative to 100 parts by weight of the total weight of the second layer.

19. The solid preparation of claim 18, further comprising an intermediate layer between said first layer and said second layer.

20. The solid preparation of claim 1, which shows each peak area ratio defined below of related substances RS1 to RS6 defined below of not more than 0.5% by high performance liquid chromatography analysis under the following conditions after one-month preservation at temperature 40° C.; humidity 22% RH, 33% RH, 44% RH or 57% RH; open state:
<conditions of high performance liquid chromatography analysis>
(1) column: Zorbax SB-CN, 5 µm, inner diameter 4.6 mm×25 cm (manufactured by Agilent)
(2) mobile phase:
mobile phase A: purified water/acetonitrile/trifluoroacetic acid=1900/100/1 (volume ratio)
mobile phase B: purified water/acetonitrile/trifluoroacetic acid=100/1900/1 (volume ratio)
(3) elution gradient program:
from 0 min to 30 min: 99/1 (mobile phase A/mobile phase B) to 75/25 (mobile phase A/mobile phase B)
from 30 min to 50 min: 75/25 (mobile phase A/mobile phase B) to 10/90 (mobile phase A/mobile phase B)
from 50 min to 51 min: 10/90 (mobile phase A/mobile phase B) to 99/1 (mobile phase A/mobile phase B)
from 51 min to 60 min: 99/1 (mobile phase A/mobile phase B) (constant)

(4) flow rate: 1 ml/min
(5) detector: UV 278 nm
(6) sample temperature: about 3° C.-about 10° C.
(7) column temperature: about 20° C.-about 30° C.
<related substances RS1-RS6>
  related substances RS1-RS6 are derived from 2-[[6-[(3R)-3-amino-1-piperidinyl]-3,4-dihydro-3-methyl-2,4-dioxo-1(2H)-pyrimidinyl]methyl]benzonitrile or a salt thereof, and show a relative elution time of 0.60±10%, 1.08±10%, 1.30±10%, 1.49±10%, 1.52±10% and 1.62±10%, respectively, when the elution time of 2-[[6-[(3R)-3-amino-1-piperidinyl]-3,4-dihydro-3-methyl-2,4-dioxo-1(2H)-pyrimidinyl]methyl]benzonitrile is 1.00, by high performance liquid chromatography analysis under the above-mentioned conditions, <peak area ratio>
peak area ratio shows the ratio of each peak area relative to the peak area at an assumed content of 2-[[6-[(3R)-3-amino-1-piperidinyl]-3,4-dihydro-3-methyl-2,4-dioxo-1(2H)-pyrimidinyl]methyl]benzonitrile as 100, in a chromatograph by high performance liquid chromatography analysis under the above-mentioned conditions.

21. The solid preparation of claim 1, wherein 2-[[6-[(3R)-3-amino-1-piperidinyl]-3,4-dihydro-3-methyl-2,4-dioxo-1(2H)-pyrimidinyl]methyl]benzonitrile or a salt thereof is physically separated from metformin hydrochloride.

22. The solid preparation of claim 1, which is a therapeutic combination drug for diabetes or obesity.

23. A method of stabilizing 2-[[6-[(3R)-3-amino-1-piperidinyl]-3,4-dihydro-3-methyl-2,4-dioxo-1(2H)-pyrimidinyl]methyl]benzonitrile or a salt thereof in a solid preparation comprising 2-[[6-[(3R)-3-amino-1-piperidinyl]-3,4-dihydro-3-methyl-2,4-dioxo-1(2H)-pyrimidinyl]methyl]benzonitrile or a salt thereof, metformin hydrochloride and an additive, which comprises physically separating 2-[[6-[(3R)-3-amino-1-piperidinyl]-3,4-dihydro-3-methyl-2,4-dioxo-1(2H)-pyrimidinyl]methyl]benzonitrile or a salt thereof from the metformin hydrochloride by the additive.

* * * * *